(12) United States Patent
Dean et al.

(10) Patent No.: US 7,026,336 B1
(45) Date of Patent: Apr. 11, 2006

(54) COMPOUNDS

(75) Inventors: David Kenneth Dean, Harlow (GB); Peter John Lovell, Harlow (GB); Andrew Kenneth Takle, Harlow (GB)

(73) Assignee: SmithKline Beecham p.l.c., Brentford (GB)

( * ) Notice: Subject to any disclaimer, the term of this patent is extended or adjusted under 35 U.S.C. 154(b) by 91 days.

(21) Appl. No.: 10/130,019

(22) PCT Filed: Nov. 20, 2000

(86) PCT No.: PCT/GB00/04413

§ 371 (c)(1), (2), (4) Date: Sep. 23, 2002

(87) PCT Pub. No.: WO01/38324

PCT Pub. Date: May 31, 2001

Related U.S. Application Data

(60) Provisional application No. 60/166,895, filed on Nov. 22, 1999, provisional application No. 60/166,886, filed on Nov. 22, 1999, provisional application No. 60/166,885, filed on Nov. 22, 1999, provisional application No. 60/166,814, filed on Nov. 22, 1999.

(51) Int. Cl.
- C07D 401/04 (2006.01)
- C07D 401/14 (2006.01)
- C07D 403/04 (2006.01)
- A61K 31/4439 (2006.01)
- A61P 9/10 (2006.01)

(52) U.S. Cl. ............ 514/341; 546/274.1; 544/317; 544/331; 544/333

(58) Field of Classification Search ......... 546/274.1; 514/341
See application file for complete search history.

(56) References Cited

U.S. PATENT DOCUMENTS

| | | |
|---|---|---|
| 3,707,475 A | 12/1972 | Lombardino |
| 4,348,404 A | 9/1982 | Whitney |
| 5,166,214 A | 11/1992 | Billheimer et al. |
| 5,179,117 A | 1/1993 | Maduckuie, Jr. |
| 5,236,917 A | 8/1993 | Dunlap et al. |
| 5,310,748 A | 5/1994 | Wilde et al. |
| 5,514,505 A | 5/1996 | Limburg et al. |
| 5,552,557 A | 9/1996 | Fujii et al. |
| 5,620,999 A | 4/1997 | Weier et al. |
| 5,656,644 A | 8/1997 | Adams et al. |
| 5,717,100 A | 2/1998 | Selnick et al. |
| 5,859,041 A | 1/1999 | Liverton et al. |
| 6,040,320 A | 3/2000 | Beers et al. |
| 6,207,687 B1 | 3/2001 | Claiborne et al. |
| 6,235,760 B1 | 5/2001 | Feuerstein |
| 6,342,510 B1 | 1/2002 | Isakson et al. |
| 6,436,966 B1 | 8/2002 | Ohkawa et al. |
| 6,548,520 B1 | 4/2003 | Adams et al. |
| 6,602,877 B1 | 8/2003 | Bamborough et al. |
| 2003/0134837 A1 | 7/2003 | Gaiba et al. |
| 2003/0153588 A1 | 8/2003 | Steadman et al. |
| 2004/0038964 A1 | 2/2004 | Dean et al. |
| 2004/0053943 A1 | 3/2004 | Adams et al. |
| 2004/0127496 A1 | 7/2004 | Dean et al. |
| 2004/0192689 A1 | 9/2004 | Dean et al. |
| 2004/0198730 A1 | 10/2004 | Dean et al. |
| 2004/0209883 A1 | 10/2004 | Bamford et al. |
| 2004/0235843 A1 | 11/2004 | Bamford et al. |
| 2004/0248896 A1 | 12/2004 | Dean et al. |
| 2004/0254186 A1 | 12/2004 | Dean et al. |

FOREIGN PATENT DOCUMENTS

| | | |
|---|---|---|
| WO | WO 97/36587 | 10/1997 |
| WO | WO 98/16227 | 4/1998 |
| WO | WO 99/01449 | 1/1999 |
| WO | WO 99/32436 | 7/1999 |
| WO | WO 99/32455 | 7/1999 |
| WO | WO 99/61437 | 12/1999 |
| WO | WO 00/01688 | 1/2000 |
| WO | WO 00/26209 | 5/2000 |
| WO | WO 00/33836 | 6/2000 |
| WO | WO 00/64422 | 11/2000 |
| WO | WO 01/37835 | 5/2001 |

OTHER PUBLICATIONS

Mercer et al. {Biochimica et Biophysica Acta 1653 (2003) 25-40}.*
Adams et al, *Bioorganic & Medical Chemistry Letters*, vol. 8 pp. 3111-3116 (1998).
Adams et al, *Current Opinion in Drug Discovery and Development*, vol. 2(2) pp. 96-109 (1999).
Antolini et al, *Bioorganic & Medical Chemistry Letters*, vol. 9 pp. 1023-1028 (1999).

(Continued)

Primary Examiner—Mark L. Berch
Assistant Examiner—Kahsay Habte
(74) Attorney, Agent, or Firm—Dara L. Dinner; Stephen Venetianer; Charles M. Kinzig

(57) ABSTRACT

Compounds of formula (I) wherein X is O, $CH_2$, S or NH, or the moiety X—$R^1$ is hydrogen; V is CH or N; Y is $NR^{10}R^{11}$, $NR^{10}C(Z)NR^{10}R^{11}$, $NR^{10}COOR^{11}$ or $NR^{10}SO_2R^{11}$; Ar is phenyl or a 5- or 6-membered heteroaryl ring either of which may be optionally substituted; n is 0, 1, 2, 3 or 4; and $R^1$, $R^2$, $R^3$, $R^4$, $R^{10}$ and $R^{11}$ have the meanings given in the description; and pharmaceutically acceptable salt thereof.

12 Claims, No Drawings

OTHER PUBLICATIONS

Astles et al, *J. Med. Chem.*, vol. 39 pp. 1423 (1996).
Bilodeau et al, *J. Org. Chem.*, vol. 63 pp. 2800-2801 (1998).
Boehm et al, *Exp Opinion Ther. Patents*, vol. 10(1) (2000).
Boehm et al, *J. Med Chem.*, vol. 39 pp. 3929-3937 (1996).
Claiborne et al, *Tetrahedron Letters*, vol. 39 pp. 8939-8942 (1998).
Cuenda A. et al, *FEBS Letters*, vol. 364 pp. 229-233 (1995).
de Laszlo et al, *Bioorganic & Medical Chemistry Letters*, vol. 8 pp. 2689-2694 (1998).
Dumas et al, *Bioorganic & Medical Chemistry Letters*, vol. 10 pp. 2047-2050 (2000).
Dumas et al, *Bioorganic & Medical Chemistry Letters*, vol. 10 2051-2054 (2000).
Eberwein et al, *Clinical Cancer Researc*, vol. 6 (Supple.) Poster session 17 pp. 4547(406) (Nov 2000).
Engel & Steglich, *Liebigs Ann. Chem.*, p. 1916 (1978).
Fischer et al., *Rec.Trav.Chim.Pays.Bas.*, vol. 84 p439 (1965).
Gallagher et al, *Bioorganic & Medical Chemistry*, vol. 5(1) pp. 49-64 (1997).
Garcia-Echeverria et al, *Med. Res. Reviews*, vol. 20(1) pp. 28-57 (2000).
Garigipati, R., *Tetrahedron Letters*, vol. 31,p. 190(1989).
Hall-Jackson et al, *Oncogene*, vol. 18 pp. 2047-2054 (1999).
Heimbrock et al, "Identification of Potent, Selective Inhibitors of Raf Protein Kinase", *Amer. Assoc for Cancer Res New Orleans* Apr. 1998.
Henry et al, *Bioorganic & Medical Chemistry Letters*, vol. 8 pp. 3335-3340 (1998).
Henry et al, *Drugs of the Future*, vol. 24(12) pp. 1345-1354 (1999).
Ishibashi, *Chem. Pharm. Bull.*, vol. 37(8), pp. 2214-2216 (1989).
Johnson, P.A., *J.Chem.Soc.*, Perkin Trans., vol. 1, pp. 895-905 (1996).
Katritzky, *Synthesis*, pp. 45-47 (1993).
Kumada et al., *Tetrahedron Letters*, vol. 22, p 5319 (1981).
Lackey et al, *Bioorganic & Medical Chemistry Letters*, vol. 10 pp. 223-226 (2000).
Lee et al, *Pharmacol Ther.*, vol. 82(2-3) pp. 389-397 (1999).
Lisnock et al, *BioChemistry*, vol. 37 pp. 16573-16581 (1998).
Liverton et al, *J. Med Chem.*, vol. 42 pp. 2180-2190 (1999).
Lowinger et al, Clinical Cancer Research, vol. 6(335) (Suppl.) Poster session 13 p. 4533 (Nov. 2000).
Morton et al., *Tetrahedron Letters*, 4123 (1982).
Pridgen, *J.Org.Chem.*, vol. 47, p. 4319 (1982).
R.P.Soni,*Aust.J.Chem.*, vol. 35, pp. 1493-6 (1982).
Revesz et al, *Bioorganic & Medical Chemistry Letters*, vol. 10 pp. 1261-1264 (2000).
Salituro et al, *Current Medicinal Chemistry*, vol. 6 pp. 807-823 (1999).
Snieckus, V., *Tetrahedron Letters*, vol. 29, 2135 (1988).
Stille, *J.Amer.Chem.Soc.*, vol. 109, p. 5478 (1978).
Stover et al, *Current Opinion in Drug Discovery and Development*, vol. 2(4) pp. 274-285 (1999).
Strzybny et al., *J. Org. Chem.*, vol. 28, p. 3381 (1963).
Terashimia, M., *Chem.Pharm.Bull.*, vol. 11, p. 4755 (1985).
Thompson, et al., *J.Org.Chem.*, vol. 49, p. 5237 (1984).
Toledo et al, *Current Medicinal Chemistry*, vol. 6 pp. 775-805 (1999).
Tong et al, *Nature Structural Biology*, vol. 4(4) p. 311 (1997).
Two Novel structural classes of p38 Kinase inhibitors, *Exp Opin. Ther. Patents* vol. 9(4) pp. 477-480 (1999).
Uno, *Bull. Chem. Soc. Japan.*, vol. 69, pp. 1763-1767 (1996).
VanLeusen et al., *J.O.C.*, vol. 42, p. 1153 (1977).
Vertex Pharmaceuticals, *Exp Opin. Ther. Patents*, vol. 10(7) pp. 1151-1154 (2000).
Wang et al, *Stucture*, vol. 6 pp. 1117-1128 (Sep. 15, 1998).
Young et al, *The Journal of Biological Chemistry*, vol. 272(18) pp. 12116-12121 (1997).
Zavyalov, et al., *Khim Farm Zh*, vol. 26(3), p. 88 (1992) (With Translation).

\* cited by examiner

COMPOUNDS

This application is the §371 national stage entry of PCT/GB00/04413, filed 20 Nov. 2000, which claims benefit from the following U.S. Provisional Applications: 60/166,814 filed 22 Nov. 1999, 60/166,886 filed 22 Nov. 1999, 60/166,885 filed 22 Nov. 1999 and 60/166,895 filed 22 Nov. 1999.

This invention relates to novel compounds and their use as pharmaceuticals particularly as Raf kinase inhibitors for the treatment of neurotraumatic diseases.

Raf protein kinases are key components of signal transduction pathways by which specific extracellular stimuli elicit precise cellular responses in mammalian cells. Activated cell surface receptors activate ras/rap proteins at the inner aspect of the plasmamembrane which in turn recruit and activate Raf proteins. Activated Raf proteins phosphorylate and activate the intracellular protein kinases MEK1 and MEK2. In turn, activated MEKs catalyse phosphorylation and activation of p42/p44 mitogen-activated protein kinase (MAPK). A variety of cytoplasmic and nuclear substrates of activated MAPK are known which directly or indirectly contribute to the cellular response to environmental change. Three distinct genes have been identified in mammals that encode Raf proteins; A-Raf, B-Raf and C-Raf (also known as Raf-1) and isoformic variants that result from differential splicing of mRNA are known.

Inhibitors of Raf kinases have been suggested for use in disruption of tumor cell growth and hence in the treatment of cancers, e.g. histiocytic lymphoma, lung adenocarcinoma, small cell lung cancer and pancreatic and breast carcinoma; and also in the treatment and/or prophylaxis of disorders associated with neuronal degeneration resulting from ischemic events, including cerebral ischemia after cardiac arrest, stroke and multi-infarct dementia and also after cerebral ischemic events such as those resulting from head injury, surgery and/or during childbirth.

PCT/EP00/03730 discloses the use of Raf kinase inhibitors in the treatment of neurotraumatic diseases.

WO 00/26209 discloses anti-inflammatory and immunosuppressant 4-phenyl-5-pyrimidinyl-imidazoles including:

- [1-[4-(4-fluorophenyl)-5-[2-(methylthio)-4-pyrimidinyl]-1H-imidazol-2-yl]cyclohexyl]-carbamic acid, phenylmethyl ester;
- [1-[4-(4-fluorophenyl)-5-[2-(methylsulfinyl)-4-pyrimidinyl]-1H-imidazol-2-yl]cyclohexyl]-carbamic acid, phenylmethyl ester;
- [1-[4-(4-fluorophenyl)-5-[2-[[(1R)-1-phenylethyl]amino]-4-pyrimidinyl]-1H-imidazol-2-yl]cyclohexyl]-carbamic acid, phenylmethyl ester;
- 4-[2-(1-aminocyclohexyl)-5-(4-fluorophenyl)-1H-imidazol-4-yl]-N-[(1R)-1-phenylethyl]-2-pyrimidinamine;
- 4-[2-(1-aminocyclohexyl)-5-(4-fluorophenyl)-1H-imidazol-4-yl]-N-[(1S)-1-phenylethyl]-2-pyrimidinamine;
- 4-[2-(1-aminocyclohexyl)-5-(4-fluorophenyl)-1H-imidazol-4-yl]-N-(3-methylphenyl)-2-pyrimidinamine;
- 4-[2-(1-amino-1-methylethyl)-5-(4-fluorophenyl)-1H-imidazol-4-yl]-N-[(1R)-1-phenylethyl]-2-pyrimidinamine; and
- 4-[2-(1-amino-1-methylethyl)-5-(4-fluorophenyl)-1H-imidazol-4-yl]-N-[(1S)-1-phenylethyl]-2-pyrimidinamine.

WO 99/01449 discloses anti-inflammatory and immunosuppressant 2-substituted 4,5-diarylimidazoles including:

- [1-[4-(4-fluorophenyl)-5-(4-pyridinyl)-1H-imidazol-2-yl]cyclohexyl]-carbamic acid, phenylmethyl ester; and
- 1-[4-(4-fluorophenyl)-5-(4-pyridinyl)-1H-imidazol-2-yl]-cyclohexanamine.

We have now found a group of novel compounds that are inhibitors of Raf kinases, in particular inhibitors of B-Raf kinase.

According to the invention there is provided a compound of formula (I):

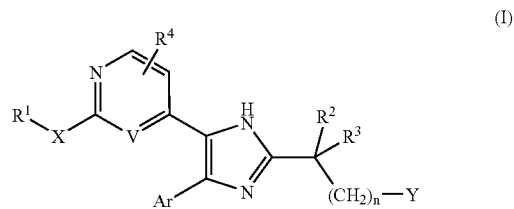

wherein
X is O, $CH_2$, S or NH, or the moiety X—$R^1$ is hydrogen;
V is CH or N;
$R^1$ is hydrogen, $C_{1-6}$alkyl, aryl, aryl$C_{1-6}$alkyl, heterocyclyl, heterocyclyl$C_{1-6}$alkyl, heteroaryl or heteroaryl$C_{1-6}$alkyl, any of which may be optionally substituted;
$R^2$ and $R^3$ independently represent optionally substituted $C_{1-6}$alkyl, or $R^2$ and $R^3$ together with the carbon atom to which they are attached form an optionally substituted $C_{3-7}$cycloalkyl, $C_{5-7}$cycloalkenyl, or 5 to 7-membered heterocyclyl ring containing up to 3 heteroatoms selected from N, O and S;
$R^4$ is hydrogen, X—$R^1$, halogen, optionally substituted $C_{1-6}$alkylsulfinyl, $CH_2OR^5$, di-$C_{1-6}$alkylamino, $N(R^6)C(O)R^7$, $N(R^6)S(O)_2R^8$ or a 5 to 7-membered N-heterocyclyl ring which optionally contains an additional heteroatom selected from O, S and $NR^9$;
Y is $NR^{10}R^{11}$, $NR^{10}C(Z)NR^{10}R^{11}$, $NR^{10}COOR^{11}$ or $NR^{10}SO_2R^{11}$;
Ar is phenyl or a 5- or 6-membered heteroaryl ring either of which may be optionally substituted;
n is 0, 1, 2, 3 or 4;
$R^5$ is hydrogen, —C(Z)$R^{12}$ or optionally substituted $C_{1-6}$alkyl, optionally substituted aryl, optionally substituted aryl$C_{1-6}$alkyl or $S(O)_2R^8$;
$R^6$ is hydrogen or $C_{1-6}$alkyl;
$R^7$ is hydrogen, $C_{1-6}$alkyl, $C_{3-7}$cycloalkyl, aryl, aryl$C_{1-6}$alkyl, heteroaryl, heteroaryl$C_{1-6}$alkyl, heterocyclyl or heterocyclyl$C_{1-6}$alkyl;
$R^8$ is $C_{1-6}$alkyl, $C_{3-7}$cycloalkyl, aryl, aryl$C_{1-6}$alkyl, heteroaryl, heteroaryl$C_{1-6}$alkyl, heterocyclyl or heterocyclyl$C_{1-6}$alkyl;
$R^9$ is hydrogen, cyano, $C_{1-4}$alkyl, $C_{3-7}$cycloalkyl or aryl;
$R^{10}$, $R^{11}$ and $R^{12}$ are independently selected from hydrogen, $C_{1-6}$alkyl, $C_{3-7}$cycloalkyl, heterocyclyl, heterocyclyl$C_{1-6}$alkyl, heterocyclyl$C_{2-6}$alkenyl, aryl, aryl$C_{1-6}$alkyl, aryl$C_{2-6}$alkenyl, heteroaryl, heteroaryl$C_{1-6}$alkyl and heteroaryl$C_{2-6}$alkenyl any of which may be optionally substituted; or $NR^{10}R^{11}$ may represent a 5 to 7-membered heterocyclyl ring optionally containing an additional heteroatom selected from O, N and S; and
Z is oxygen or sulfur;
or a pharmaceutically acceptable salt thereof;
provided that the compound of formula (I) is not:

i) [1-[4-(4-fluorophenyl)-5-[2-(methylthio)-4-pyrimidinyl]-1H-imidazol-2-yl]cyclohexyl]-carbamic acid, phenylmethyl ester;

ii) [1-[4-(4-fluorophenyl)-5-[2-(methylsulfinyl)-4-pyrimidinyl]-1H-imidazol-2-yl]cyclohexyl]-carbamic acid, phenylmethyl ester;
iii) [1-[4-(4-fluorophenyl)-5-[2-[[(1R)-1-phenylethyl]amino]-4-pyrimidinyl]-1H-imidazol-2-yl]cyclohexyl]-carbamic acid, phenylmethyl ester;
iv) 4-[2-(1-aminocyclohexyl)-5-(4-fluorophenyl)-1H-imidazol-4-yl]-N-[(1R)-1-phenylethyl]-2-pyrimidinamine;
v) 4-[2-(1-aminocyclohexyl)-5-(4-fluorophenyl)-1H-imidazol-4-yl]-N-[(1S)-1-phenylethyl]-2-pyrimidinamine;
vi) 4-[2-(1-aminocyclohexyl)-5-(4-fluorophenyl)-1H-imidazol-4-yl]-N-(3-methylphenyl)-2-pyrimidinamine;
vii) 4-[2-(1-amino-1-methylethyl)-5-(4-fluorophenyl)-1H-imidazol-4-yl]-N-[(1R)-1-phenylethyl]-2-pyrimidinamine;
viii) 4-[2-(1-amino-1-methylethyl)-5-(4-fluorophenyl)-1H-imidazol-4-yl]-N-[(1S)-1-phenylethyl]-2-pyrimidinamine;
ix) [1-[4-(4-fluorophenyl)-5-(4-pyridinyl)-1H-imidazol-2-yl]cyclohexyl]-carbamic acid, phenylmethyl ester; or
x) 1-[4-(4-fluorophenyl)-5-(4-pyridinyl)-1H-imidazol-2-yl]-cyclohexanamine.

Alkyl and alkenyl groups referred to herein, individually or as part of larger groups e.g. alkoxy, may be straight or branched groups containing up to six carbon atoms and are optionally substituted by one or more groups selected from the group consisting of aryl, heteroaryl, heterocyclyl, $C_{1-6}$alkoxy, halo$C_{1-6}$alkoxy, $C_{1-6}$alkylthio, aryloxy, aryl$C_{1-6}$alkoxy, aryl$C_{1-6}$alkylthio, amino, mono- or di-$C_{1-6}$alkylamino, cycloalkyl, cycloalkenyl, carboxy and esters thereof, amide, ureido, guanidino, $C_{1-6}$alkylguanidino, amidino, $C_{1-6}$alkylamidino, $C_{1-6}$acyloxy, azido, hydroxy, and halogen, and combinations thereof. Suitable combinations of substituents include those illustrated in the examples e.g. for the groups $R^{10}$ and $R^{11}$.

Cycloalkyl and cycloalkenyl groups referred to herein, unless otherwise defined, include groups having from three to eight ring carbon atoms and are optionally substituted as described above for alkyl and alkenyl groups.

When used herein, the term "aryl" means single and fused rings suitably containing from 4 to 7, preferably 5 or 6, ring atoms in each ring, which rings, may each be unsubstituted or substituted by, for example, up to three substituents. A fused ring system may include aliphatic rings and need include only one aromatic ring. Suitable aryl groups include phenyl and naphthyl such as 1-naphthyl or 2-naphthyl.

When used herein the term "heterocyclyl" suitably includes, unless otherwise defined, non-aromatic, single and fused, rings suitably containing up to four heteroatoms in each ring, each of which is selected from O, N and S, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring. Examples of heterocyclyl groups include pyrrolidine, piperidine, piperazine, morpholine, imidazolidine and pyrazolidine.

When used herein, the term "heteroaryl" suitably includes, unless otherwise defined, mono- and bicyclic heteroaromatic ring systems comprising up to four, preferably 1 or 2, heteroatoms each selected from O, N and S. Each ring may have from 4 to 7, preferably 5 or 6, ring atoms. A bicyclic heteroaromatic ring system may include a carbocyclic ring. Examples of heteroaryl groups include pyrrole, quinoline, isoquinoline, pyridine, pyrimidine, furan, thiophene, oxazole, thiazole, thiadiazole, triazole, imidazole and benzimidazole.

Aryl, hererocyclyl and heteroaryl groups may be optionally substituted by preferably up to three substituents. Suitable substituents include halogen, $C_{1-6}$-alkyl, aryl, aryl$C_{1-6}$alkyl, $C_{1-6}$alkoxy, $C_{1-6}$alkoxy$C_{1-6}$alkyl, halo$C_{1-6}$alkyl, halo$C_{1-6}$alkoxy, aryloxy, aryl$C_{1-6}$alkoxy, hydroxy, nitro, cyano, azido, amino, mono- and di-N-$C_{1-6}$alkylamino, acylamino, arylcarbonylamino, acyloxy, carbonylamino, acyloxy, carboxy, carboxy salts, carboxy esters, carbamoyl, mono- and di-N-$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkylsulphinyl, $C_{1-6}$alkylsulphonyl, heterocyclyl, heteroaryl, heterocyclyl$C_{1-6}$alkyl and heteroaryl$C_{1-6}$alkyl, and combinations thereof. Suitable combinations of substituents include those illustrated in the examples e.g. for the groups $R^{10}$ and $R^{11}$. In addition, two adjacent ring carbon atoms may be linked to form a bicyclic system.

In the compounds of formula (I):

X is preferably NH or X—$R^1$ is hydrogen and when X is NH, $R^1$ is preferably hydrogen.

When V is CH, X—$R^1$ is preferably hydrogen.

When V is N, X—$R^1$ is preferably $NH_2$.

$R^2$ and $R^3$ preferably independently represent optionally substituted $C_{1-6}$alkyl, or $R^2$ and $R^3$ together with the carbon atom to which they are attached form an optionally substituted $C_{3-7}$cycloalkyl or $C_{5-7}$cycloalkenyl ring. More preferably $R^2$ and $R^3$ represent $C_{1-6}$alkyl, or $R^2$ and $R^3$ together with the carbon atom to which they are attached form an optionally substituted $C_{3-7}$cycloalkyl ring. In particular $R^2$ and $R^3$ represent methyl.

$R^4$ is preferably hydrogen.

Ar is preferably optionally substituted phenyl.

Preferred substituents for the group Ar include halo, hydroxy, hydroxy$C_{1-6}$alkyl e.g. methyl, and $C_{1-6}$alkoxy e.g. methoxy, more preferred are halo and hydroxy. When Ar is phenyl the substituents are preferably present in the 3-position or the 3,4-positions. When Ar is phenyl it preferably has a 3-hydroxy substituent. Particular substitution patterns for Ar when phenyl are 3-hydroxy, 3-hydroxy-4-halo e.g. 3-hydroxy-4-chloro or 3-hydroxy-4-bromo, 3-hydroxy-4-methyl and 3-hydroxy-4-methoxy, more particularly 3-hydroxy-4-chloro.

n is preferably 0 or 1, more preferably n is 1.

Y is preferably $NR^{10}R^{11}$.

$R^{10}$ is preferably hydrogen.

$R^{11}$ is preferably $C_{1-6}$alkyl, $C_{3-7}$cycloalkyl, heterocyclyl, heterocyclyl$C_{1-6}$alkyl, heterocyclyl$C_{2-6}$alkenyl, aryl, aryl$C_{1-6}$alkyl, aryl$C_{2-6}$alkenyl, heteroaryl, heteroaryl$C_{1-6}$alkyl or heteroaryl$C_{2-6}$alkenyl, any of which may be optionally substituted.

The compounds of formula (I) preferably have a molecular weight or less than 800.

Particular compounds according to the invention include those mentioned in the examples and their pharmaceutically acceptable salts.

It will be appreciated that for use in medicine the salts of the compounds of formula (I) should be pharmaceutically acceptable. Suitable pharmaceutically acceptable salts will be apparent to those skilled in the art and include those described in *J. Pharm. Sci.*, 1977, 66, 1–19, such as acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amounts of water.

The invention extends to all isomeric forms including stereoisomers and geometric isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Compounds of formula (I) are imidazole derivatives which may be readily prepared using procedures well-known to those skilled in the art, and described in, for instance, Comprehensive Heterocyclic Chemistry, Editors Katrizky and Rees, Pergamon Press, 1984, 5, 457–497, from starting materials which are either commercially available or can be prepared from such by analogy with well-known processes. A key step in many such syntheses is the formation of the central imidazole nucleus, to give compounds of formula (I). Suitable procedures are described in inter alia U.S. Pat. No. 3,707,475 and U.S. Pat. No. 3,940,486. These patents describe the synthesis of α-diketones and α-hydroxyketones (benzoins) and their subsequent use in preparing imidazoles and N-hydroxyl imidazoles.

product. Heating the diketone with an aldehyde and ammonium acetate in acetic acid allows access to the imidazole nucleus. Thereafter, the group $Y_1$ may be converted into a group Y using conventional functional group interconversion procedures. Functional group transformations are well known in the art and are described in, for instance, *Comprehensive Organic Functional Group Transformations*, eds. A. R. Katritzky, O. Meth-Cohn, and C. W. Rees (Elsevier Science Ltd., Oxford, 1995), *Comprehensive Organic Chemistry*, eds. D. Barton and W. D. Ollis (Pergamon Press, Oxford, 1979), and *Comprehensive Organic Transformations*, R. C. Larock (VCH Publishers Inc., New York, 1989). the group $Y_1$ is preferably $(CH_2)_nNH_2$ or a protected form thereof e.g. $(CH_2)_nNHBoc$.

During the synthesis of the compounds of formula (I) labile functional groups in the intermediate compounds, e.g. hydroxy, carboxy and amino groups, may be protected. A comprehensive discussion of the ways in which various labile functional groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991).

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable salts thereof.

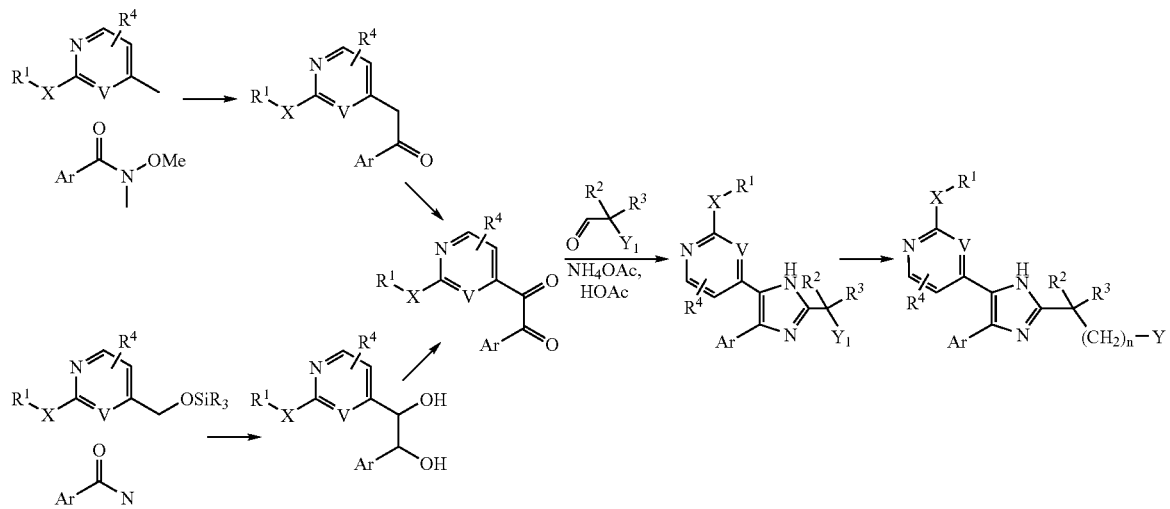

Preferred methods for preparing compounds of this invention are as outlined in the above scheme. α-Diketones are prepared by condensation of the anion of, for example, a 4-substituted pyridine derivative (V=CH, X—$R^1$=H and $R^4$=H) with the Weinreb amide of an aryl acid or an aryl-aldehyde, followed by oxidation of the intermediate Pharmaceutically acceptable salts may be prepared conventionally by reaction with the appropriate acid or acid derivative.

As indicated above the compounds of formula (I) and their pharmaceutically acceptable salts are useful the treatment and/or prophylaxis of disorders in which Raf kinases, in particular B-Raf kinase, are implicated.

According to a further aspect of the invention there is provided the use of a compound of formula (I) or a pharmaceutically acceptable salt thereof, but without provisos i) to x), as an inhibitor of B-Raf kinase.

As indicated above the compounds of formula (I) and their pharmaceutically acceptable salts are useful for the treatment and/or prophylaxis of disorders associated with neuronal degeneration resulting from ischemic events.

According to a further aspect of the invention there is provided a method of treatment or prophylaxis of a neurotraumatic disease, in a mammal in need thereof, which comprises administering to said mammal an effective amount of a compound of formula (I) or a pharmaceutically acceptable salt thereof, but without provisos i) to x).

According to a further aspect of the invention there is provided the use of a compound of formula (I) or a pharmaceutically acceptable salt thereof, but without provisos i) to x), in the manufacture of a medicament for the prophylactic or therapeutic treatment of any disease state in a human, or other mammal, which is exacerbated or caused by a neurotraumatic event.

Neurotraumatic diseases/events as defined herein include both open or penetrating head trauma, such as caused by surgery, or a closed head trauma injury, such as caused by an injury to the head region. Also included within this definition is ischemic stroke, particularly to the brain area, transient ischemic attacks following coronary by-pass and cognitive decline following other transient ischemic conditions.

Ischemic stroke may be defined as a focal neurologic disorder that results from insufficient blood supply to a particular brain area, usually as a consequence of an embolus, thrombi, or local atheromatous closure of the blood vessel. Roles for stress stimuli (such as anoxia), redox injury, excessive neuronal excitatory stimulation and inflammatory cytokines in this area has been emerging and the present invention provides a means for the potential treatment of these injuries. Relatively little treatment, for acute injuries such as these has been available.

The compounds of the invention may also be used in the treatment or prophylaxis of cancers.

The compounds of the invention may also be of use for the treatment or prophylaxis of CSBP/p38 mediated diseases as described in WO 99/01131 and WO 99/01130.

In order to use the compounds of formula (I) in therapy, they will normally be formulated into a pharmaceutical composition in accordance with standard pharmaceutical practice.

According to a further aspect of the invention there is provided a pharmaceutical composition comprising a compound of formula (I) or a pharmaceutically acceptable salt thereof and a pharmaceutically acceptable carrier.

The compounds of formula (I) may conveniently be administered by any of the route conventionally used for drug administration, for instance, parenterally, orally, topically or by inhalation. The compounds of formula (I) may be administered in conventional dosage forms prepared by combining them with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier is dictated by the amount of compound of formula (I) with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule, in powder or pellet form or in the form of a troche or lozenge. The amount of solid carrier will vary widely but preferably will be from about 25 mg to about 1 g. When a liquid carrier is used, the preparation may be in the form of a syrup, emulsion, soft gelatin capsule, sterile injectable liquid such as an ampoule or nonaqueous liquid suspension.

The compounds of formula (I) are preferably administered parenterally, that is by intravenous, intramuscular, subcutaneous intranasal, intrarectal, intravaginal or intraperitoneal administration. The intravenous form of parenteral administration is generally preferred. The compounds may be administered as a bolus or continuous infusion e.g. over 3 days. Appropriate dosage forms for such administration may be prepared by conventional techniques.

The compounds of formula (I) may also be administered orally. Appropriate dosage forms for such administration may be prepared by conventional techniques.

The compounds of formula (I) may also be administered by inhalation, that is by intranasal and oral inhalation administration. Appropriate dosage forms for such administration, such as aerosol formulations, may be prepared by conventional techniques.

The compounds of formula (I) may also be administered topically, that is by non-systemic administration. This includes the application of the inhibitors externally to the epidermis or the buccal cavity and the instillation of such a compound into the ear, eye and nose, such that the compound does not significantly enter the blood stream.

For all methods of use disclosed herein the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of the inhibitors will be determined by the nature and extent of the condition being treated, the form, route and site of administration, and the particular patient being treated, and that such optimums can be determined by conventional techniques. It will also be appreciated by one of skill in the art that the optimal course of treatment, i.e. the number of doses of the inhibitors given per day for a defined number of days, can be ascertained by those skilled in the art using conventional course of treatment determination tests. In the case of pharmaceutically acceptable salts the above figures are calculated as the parent compound of formula (I).

No toxicological effects are indicated/expected when a compound of formula (I) is administered in the above mentioned dosage range.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention.

Example 1

(2-(4-(4-Chloro-3-methoxy-phenyl)-5-pyridin-4-yl-1H-imidazol-2-yl)-2-methyl-propyl)-carbamic acid tert-butyl ester

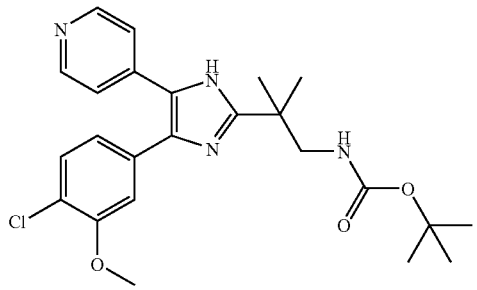

Step 1. 4-Chloro-3,N-dimethoxy-N-methyl-benzamide

A suspension of 4-chloro-3-methoxybenzoic acid (D. Claudi et al *J. Med. Chem.*, 1992, 35, 4408) (37.2 g, 0.2 mol) in dichloromethane (500 ml) containing oxalyl chloride (26 ml) was treated with N,N-dimethylformamide (10 drops). After stirring at room temperature for 6 hours the solution was concentrated at reduced pressure, additional dichloromethane added to the residue and the solvent re-evaporated. The residue was then dissolved in acetonitrile (600 ml) and methoxymethylamine hydrochloride (20.5 g, 0.21 mol) added. The mixture was cooled in an ice-bath, a solution of pyridine (80 ml) in acetonitrile (150 ml) added dropwise and the mixture stirred at room temperature for 18 hours. The solution was then concentrated and the residue partitioned between ethyl acetate and saturated potassium carbonate solution. The organic layer was separated, washed with brine, dried over anhydrous magnesium sulphate, filtered and concentrated at reduced pressure, then the residue re-evaporated with toluene to give the title compound (40.0 g, 87%) as a colourless oil; MS(ES+) m/e 230/232 [M+H]+.

Step 2. 1-(4-Chloro-3-methoxy-phenyl)-2-pyridin-4-yl-ethanone

4-Picoline (16.9 ml, 0.174 mol) was added dropwise to a stirred solution of lithium di-isopropylamide (110 ml, 0.22 mol, 2M solution in heptane, ethylbenzene, tetrahydrofuran) in dry tetrahydrofuran (150 ml) at −78° C. After stirring at −78° C. for 15 min a solution of the product of Step 1 (40.0 g, 0.174 mol) in tetrahydrofuran (100 ml) was added dropwise and the reaction allowed to warm to room temperature over 3 hours. The solution was then cooled in ice, saturated ammonium chloride solution added and the aqueous mixture extracted with ethyl acetate. The combined organic extracts were then washed with brine, dried over anhydrous magnesium sulphate, filtered and concentrated at reduced pressure. The resulting gum was triturated with cold diethyl ether/hexane (1:1, 300 ml) and the solid collected to give the title compound as a pale yellow solid (29 g, 64%); MS(ES+) m/e 262/264 [M+H]+.

Step 3. 1-(4-Chloro-3-methoxy-phenyl)-2-pyridin-4-yl-ethane-1,2-dione

A solution of the product of Step 2 (22.5 g, 86 mmol) in dimethylsulphoxide (150 ml) was stirred at 55° C. Hydrogen bromide (48% aqueous, 21 ml) was added dropwise and the solution was heated at 55° C. for 1 hour. After cooling to room temperature the solution was poured into a solution of sodium acetate (21 g) in ice-water (1000 ml) and the resulting slurry was stirred at room temperature for 30 min. The mixture was extracted with ethyl acetate and the organic layers were combined, washed with brine, dried over anhydrous magnesium sulphate, filtered and concentrated at reduced pressure. The residue was triturated with diethyl ether/hexane (1:4) and the solid collected to give the title compound as a yellow solid; MS(EI) m/e 275/277 [M]+.

Step 4. (2-(4-(4-Chloro-3-methoxy-phenyl)-5-pyridin-4-yl-1H-imidazol-2-yl)-2-methyl-propyl)-carbamic acid tert-butyl ester The product of Step 3 (275 mg, 1 mmol), (2,2-dimethyl-3-oxo-propyl)-carbamic acid tert-butyl ester (Y. Guindon et al., *J. Am. Chem. Soc.*, 1997, 119, 9289) (250 mg, 1.25 mmol) and ammonium acetate (770 mg, 10 mmol) were dissolved in acetic acid (5 ml) and heated to reflux for 1 hour, then allowed to cool to room temperature. The reaction mixture was poured into a mixture of ammonium hydroxide (10 ml) and ice. The mixture was extracted with ethyl acetate, the organic layers were combined, washed with brine, dried over anhydrous magnesium sulphate, filtered and concentrated at reduced pressure. The residue was chromatographed on silica gel eluting with ethyl acetate to give the title compound as a pale yellow solid (172 mg, 38%); MS(ES+) m/e 457/459 [M+H]+.

Example 2

2-(4-(4-Chloro-3-methoxy-phenyl)-5-pyridin-4-yl-1H-imidazol-2-yl)-2-methyl-propylamine

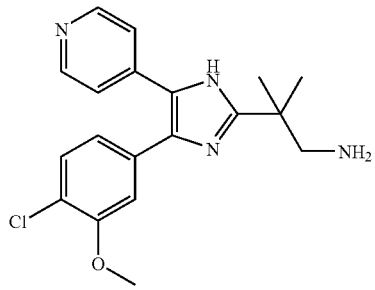

A solution of Example 1 (112 mg, 0.245 mmol) in dichloromethane (2 ml) containing trifluoroacetic acid (1 ml) was stirred at room temperature for 3 hours. The solution was concentrated at reduced pressure and the residue was partitioned between saturated sodium hydrogen carbonate solution and ethyl acetate. The organic layers were then combined, washed with brine, dried over anhydrous magnesium sulphate, filtered and concentrated at reduced pressure to give the title compound (59 mg, 68%) as a solid; MS(ES+) m/e 357/359 [M+H]+.

Example 3

5-(2-(2-Amino-1,1-dimethyl-ethyl)-5-pyridin-4-yl-1H-imidazol-4-yl)-2-chloro-phenol

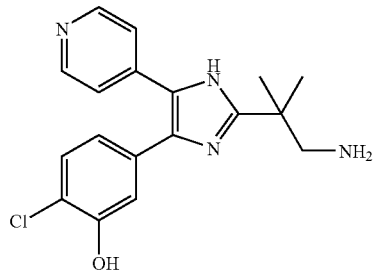

A solution of Example 2 (356 mg, 1 mmol) in dichloromethane (20 ml) cooled to 5° C. was treated with boron tribromide (1M in dichloromethane, 5 ml) followed by additional dichloromethane (10 ml). The solution was stirred at 5° C. for 2 hours then at room temperature for a further 2 hours. 2M hydrochloric acid (1 ml) and water (5 ml) were then added and the reaction heated to 50° C. for 15 min. After cooling the mixture was neutralised with 15% sodium hydroxide solution and the resultant precipitate collected by filtration to afford the title compound as a yellow solid (206 mg, 60%); MS(ES+) m/e 343/345 [M+H]+.

Example 4

N-(2-(4-(4-Chloro-3-methoxyphenyl)-5-pyridin-4-yl-1H-imidazol-2-yl)-2-methylpropyl)methane-sulfonamide

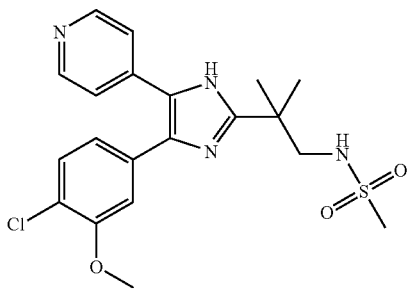

A solution of Example 2 (178 mg, 0.5 mmol) in dichloromethane (10 ml) containing pyridine (0.12 ml, 1.5 mmol) at 0° C. was treated with a solution of methanesulfonyl chloride (57.3 mg, 0.5 mmol) in dichloromethane (1 ml). The solution was stirred at 0° C. for 1 hour followed by 30 min at room temperature before being diluted with dichloromethane and saturated sodium hydrogen carbonate solution. The aqueous layer was then separated and extracted with additional dichloromethane. The combined organic extracts were washed with brine, dried over anhydrous magnesium sulphate, filtered and concentrated at reduced pressure. The residue was chromatographed on silica gel eluting with dichloromethane/methanol/0.880 ammonia solution (8:1:0.1) to give the title compound (85 mg, 40%) as a pale yellow solid; MS(ES+) m/e 435/437 [M+H]+.

Example 5

(2-(4-(3,4-Dihloro-phenyl)-5-pyridin-4-yl-1H-imidazol-2-yl)-2-methyl-propyl)-carbamic acid tert-butyl ester

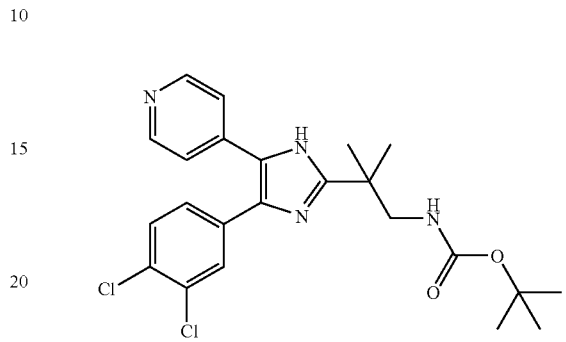

Step 1. 1-(3,4-Dichlorophenyl)-2-pyridin-4-yl-ethane-1,2-diol 4-(tert-Butyldimethylsilyloxymethyl)-pyridine (67 g, 0.3 mol) was dissolved in THF (250 ml) and cooled to −40° C. The solution was then treated with a 2M solution of lithium diisopropylamide in THF (200 ml, 0.4 mol) and stirred for 45 min maintaining a temperature of −40 to −20° C. The reaction mixture was maintained at −40° C. and treated dropwise with a solution of 3,4-dichlorobenzaldehyde (55.13 g, 0.32 mol) in THF (250 ml). The mixture was then stirred at room temperature for 18 hours. After cooling to 0° C. the reaction was quenched with saturated ammonium chloride solution (500 ml), and the resulting two phase mixture separated. The aqueous phase was extracted three times with ethyl acetate and the combined organics concentrated under reduced pressure. The residue was dissolved in ethyl acetate, washed with saturated sodium hydrogen carbonate solution, water and brine, dried over anhydrous magnesium sulfate and concentrated under reduced pressure to an oil (129 g). The oil was dissolved in THF (300 ml) and a 1M solution of tetrabutylammonium fluoride (360 ml, 0.36 mol) added dropwise. The solution was stirred at room temperature for 45 min, then concentrated to an oil under reduced pressure. The oil was dissolved in ethyl acetate and washed with saturated sodium bicarbonate solution, water and brine, dried over anhydrous magnesium sulfate and evaporated under reduced pressure. The oil was triturated with hexane and the resulting solid filtered and washed with hexane to afford the title compound (67.58 g 79%) as a tan solid; MS(AP+) m/e 284/286/288 [M+H]+.

Step 2. 1-(3,4-Dichlorophenyl)-2-pyridin-4-yl-ethane-1,2-dione

Dimethylsulfoxide (37 ml, 0.53 mol) was dissolved in dichloromethane (250 ml) and cooled to −78° C. Oxalyl chloride (34.5 ml, 0.40 mol) was added dropwise and the solution stirred for 20 min. A solution of the product of Step 1 (34 g, 0.12 mol) in dimethylsulfoxide (40 ml) and dichloromethane (200 ml) was added dropwise at −78° C., and the solution stirred for 30 min. Triethylamine (104 ml, 0.74 mol) was added dropwise and the solution became flocculent such that overhead stirring became necessary. The solution was allowed to stir at room temperature over 2 hours then was poured on to ice/saturated sodium hydrogen carbonate solution. The aqueous layer was separated, and re-extracted with dichloromethane. The combined organic phases were concentrated under reduced pressure to a green-yellow solid. The solid was redissolved in dichloromethane and washed with water and brine, dried over anhydrous magnesium sulfate and evaporated to a solid. The crude solid was purified by silica gel chromatography eluting with dichloromethane, to afford the title compound (28.6 g, 85%) as a yellow solid; MS(-ve ion) m/e 279/281/283 [M–H]–.

Step 3. (2-(4-(3,4-Dihloro-phenyl)-5-pyridin-4-yl-1H-imidazol-2-yl)-2-methyl-propyl)-carbamic acid tert-butyl ester The title compound (2.45 g, 27%) was prepared from the product of Step 2 and (2,2-dimethyl-3-oxo-propyl)-carbamic acid tert-butyl ester using the method described in Example 1 Step 4; MS(ES+) m/e 461/463/465 [M+H]+.

Example 6

2-(4-(3,4-Dichloro-phenyl)-5-pyridin-4-yl-1H-imidazol-2-yl)-2-methyl-propylamine

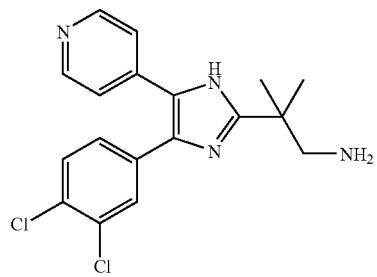

The title compound (1.34 g, 78%) was prepared from Example 5 using the method described in Example 2; MS(ES+) m/e 361/363/365 [M+H]+.

Example 7

1-(2-(4-(4-Chloro-3-hydroxy-phenyl)-5-pyridin-4-yl-1H-imidazol-2-yl)-2-methyl-propyl)-3-(4-chlorophenyl)-urea

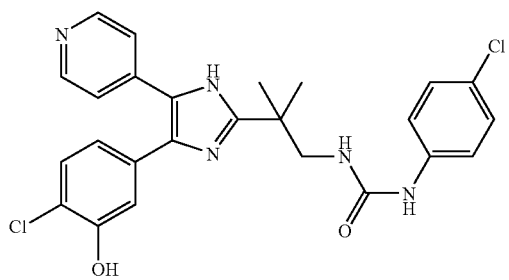

A solution of 4-chlorophenylisocyanate (46 mg, 0.3 mmol) in dichloromethane (5 ml) was treated with a solution of Example 3 (103 mg, 0.3 mmol) in methanol (1 ml). After stirring at room temperature for 30 min the solution was concentrated under reduced pressure and the residue chromatographed on silica gel eluting with dichloromethane/ methanol (10:1) to the give the title compound (72 mg, 48%) as a pale yellow solid; MS(ES+) m/e 496/498/500 [M+H]+.

Example 8

1-(2-(4-(3,4-Dichloro-phenyl)-5-pyridin-4-yl-1H-imidazol-2-yl)-2-methyl-propyl)-3-(4-chlorophenyl)-urea

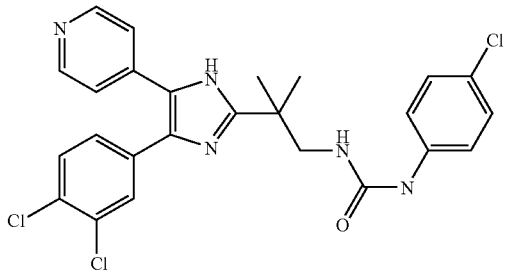

The title compound was prepared from Example 6 and 4-chlorophenylisocyanate using the method described in Example 7; MS(ES+) m/e 514/516/518 [M+H]+.

Example 9

5-(2-(2-Benzylamino-1,1-dimethyl-ethyl)-5-pyridin-4-yl-1H-imidazol-4-yl)-2-chloro-phenol

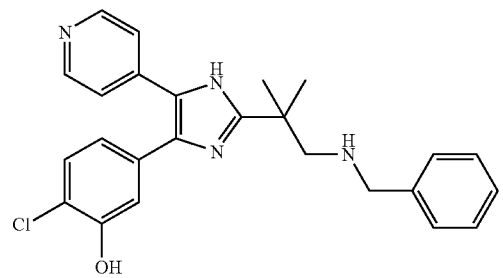

A solution of Example 3 (103 mg, 0.3 mmol) and benzaldehyde (30.7 mg, 0.3 mmol) in methanol (1 ml) was stirred at room temperature for 30 min. Sodium triacetoxyborohydride (76.3 mg, 0.36 mmol) was then added and the mixture stirred at room temperature for 3 hours before being diluted with ethyl acetate and sodium hydrogen carbonate solution. The aqueous layer was separated and re-extracted with additional ethyl acetate. The combined organic layers was then washed with brine, dried over anhydrous magnesium sulphate, filtered and concentrated under reduced pressure. The residue was chromatographed on silica gel eluting with dichloromethane/methanol/0.880 ammonia solution (20:1:0.1) to give the title compound (22 mg, 17%) as a pale yellow solid; MS(ES+) m/e 433/435 [M+H]+.

Example 10

Benzyl-(2-(4-(3,4-dichloro-phenyl)-5-pyridin-4-yl-1H-imidazol-2-yl)-2-methyl-propyl)-amine

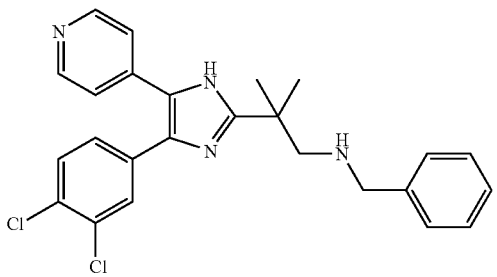

The title compound was prepared from Example 6 and benzaldehyde using the method described in Example 9; MS(ES+) m/e 451/453/455 [M+H]+.

Example 11

N-(2-(4-(3,4-Dichloro-phenyl)-5-pyridin-4-yl-1H-imidazol-2-yl)-2-methylpropyl)methanesulfonamide

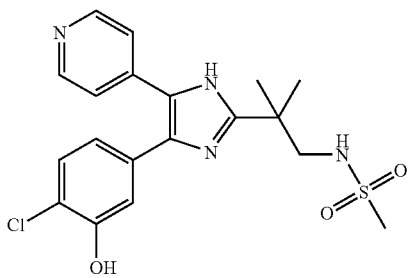

A solution of methanesulfonyl chloride (33 mg, 0.3 mmol) in dichloromethane (4 ml) was treated with a solution of Example 3 (103 mg, 0.3 mmol) in methanol (1 ml). The mixture was stirred at room temperature for 2 hours then diluted with dichloromethane and sodium hydrogen carbonate solution. The aqueous layer was then separated and extracted with additional dichloromethane. The combined organic layers were then washed with brine, dried over anhydrous magnesium sulphate, filtered and concentrated at reduced pressure. The residue was chromatographed on silica gel eluting with dichloromethane/methanol/0.880 ammonia solution (10:1:0.1) to give the title compound (16 mg, 13%) as a pale yellow solid; MS(ES+) m/e 421/423 [M+H]+.

Examples 12–34

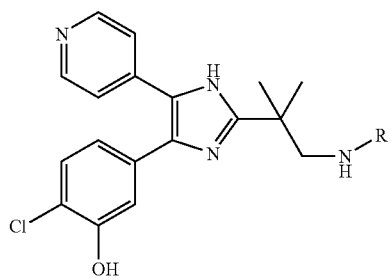

Examples 12–34 were prepared by the following general procedure. A mixture of the product of Example 3 (100 mg, 0.29 mmol), the specified aldehyde (0.32 mmol) and polymer bound trimethylammonium cyanoborohydride (125 mg, 0.5 mmol, 4 mmol/g) in methanol (3 ml) containing glacial acetic acid (0.5 ml) was stirred at room temperature for 24 hours. The reaction was then filtered, the filtrate concentrated in vacuo and the product purified by silica gel chromatography.

| Example No. | Name | R | Aldehyde | Mass spec MS(AP+) m/e[M + H]+ |
|---|---|---|---|---|
| 12 | 2-Chloro-5-{2-[2-(4-methoxy-benzylamino)-1,1-dimethyl-ethyl]-5-pyridin-4-yl-1H-imidazol-4-yl}-phenol | 4-methoxybenzyl | 4-Methoxybenzaldehyde | 463/465 |
| 13 | 2-Chloro-5-{2-[2-(4-chloro-benzylamino)-1,1-dimethyl-ethyl]-5-pyridin-4-yl-1H-imidazol-4-yl}-phenol | 4-chlorobenzyl | 4-Chlorobenzaldehyde | 467/ 469/ 471 |
| 14 | 2-Chloro-5-{2-[2-(2,2-dimethyl-propylamino)-1,1-dimethyl-ethyl]-5-pyridin-4-yl-1H-imidazol-4-yl}-phenol | CH2tBu | 2,2-Dimethyl-propionaldehyde | 413/415 |

-continued

| Example No. | Name | R | Aldehyde | Mass spec MS(AP+) m/e[M + H]+ |
|---|---|---|---|---|
| 15 | 2-Chloro-5-(2-{2-[3-(4-dimethylamino-phenyl)-allylamino]-1,1-dimethyl-ethyl}-5-pyridin-4-yl-1H-imidazol-4-yl)-phenol | 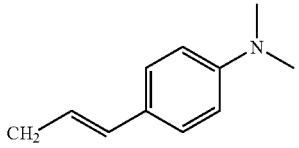 | 3-(4-Dimethyl-amino-phenyl)-propenal | 502/504 |
| 16 | 2-Chloro-5-[2-(1,1-dimethyl-2-pentylamino-ethyl)-5 pyridin-4-yl-1H-imidazol-4-yl]-phenol | | | |
| 17 | 2-Chloro-5-(2-{2-[4-(3-dimethylamino-propoxy)-benzylamino]-1,1-dimethyl-ethyl}-5-pyridin-4-yl-1H-imidazol-4-yl)-phenol | 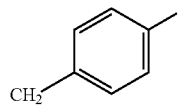 | 4-(3-Dimethylamino-propoxy)-benzaldehyde | 534/536 |
| 18 | 2-Chloro-5-{2-[2-(3,4-difluorobenzylamino)-1,1-dimethyl-ethyl]-5-pyridin-4-yl-1H-imidazol-4-yl}-phenol | 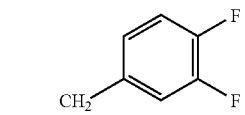 | 3,4-Difluorobenzaldehyde | 469/471 |
| 19 | 2-Chloro-5-{2-[2-(3-methoxy-benzylamino)-1,1-dimethyl-ethyl]-5-pyridin-4-yl-1H-imidazol-4-yl}-phenol | 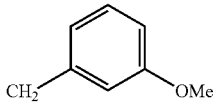 | 3-Methoxybenzadehyde | 463/465 |
| 20 | 2-Chloro-5-{2-[2-(3,4-dichloro-benzylamino)-1,1-dimethyl-ethyl]-5-pyridin-4-yl-1H-imidazol-4-yl}-phenol | 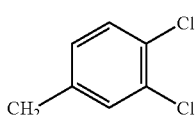 | 3,4-Dichlorobenzaldehyde | 501/503/505/507 |
| 21 | 2-Chloro-5-{2-[2-(4-methanesulfonyl-benzylamino)-1,1-dimethyl-ethy]-5-pyridin-4-yl-1H-imidazol-4-yl}-phenol | 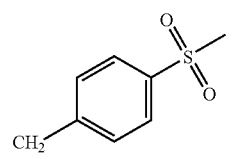 | 4-Methanesulfonyl-benzaldehyde | 511/513 |
| 22 | 2-Chloro-5-{2-[1,1-dimethyl-2-(4-trifluoromethyl-benzylamino)-ethyl]-5-pyridin-4-yl-1H-imidazol-4-yl}-phenol | 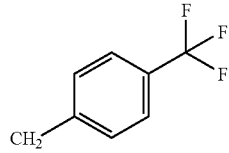 | 4-Trifluoromethyl benzaldehyde | 501/503 |
| 23 | 2-Chloro-5-(2-{2-[(furan-3-ylmethyl)amino]-1,1-dimethyl-rthyl}-5-pyridin-4-yl-1H-imidazol-4-yl)-phenol | 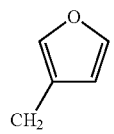 | Furan-3-carbaldehyde | 423/425 |

-continued

| Example No. | Name | R | Aldehyde | Mass spec MS(AP+) m/e[M + H]+ |
|---|---|---|---|---|
| 24 | 2-Chloro-5-(2-{1,1-dimethyl-2-[(1-methyl-1H-pyrrol-2-ylmethyl)-amino]-ethyl}-5-pyridin-4-yl-1H-imidazol-4-yl)-phenol | CH₂—(1-methyl-pyrrol-2-yl) | 1-Methyl-1H-pyrrole-2-carbaldehyde | 436/438 |
| 25 | 2-Chloro-5-(2-{1,1-dimethyl-2-[(thiazol-2-ylmethyl)-amino]-ethyl}-5-pyridin-4-yl-1H-imidazol-4-yl)-phenol | CH₂—(thiazol-2-yl) | Thiazole-2-carbaldehyde | 440/442 |
| 26 | 2-Chloro-5-(2-{1,1-dimethyl-2-[(thiophen-2-ylmethyl)-amino]-ethyl}-5-pyridin-4-yl-1H-imidazol-4-yl)-phenol | CH₂—(thiophen-2-yl) | Thiophene-2-carbaldehyde | 439/441 |
| 27 | 2-Chloro-5-{2-[1,1-dimethyl-2-(4-pyrrolidin-1-yl-benzylamino)-ethyl]-5-pyridin-4-yl-1H-imidazol-4-yl}-phenol | CH₂—(4-pyrrolidin-1-yl-phenyl) | 4-Pyrrolidin-1-yl-benzaldehyde | 502/504 |
| 28 | 2-Chloro-5-(2-{1,1-dimethyl-2-[(pyridin-3-ylmethyl)-amino]-ethyl}-5-pyridin-4-yl-1H-imidazol-4-yl)-phenol | CH₂—(pyridin-3-yl) | Pyridine-3-carbaldehyde | 434/436 |
| 29 | 2-Chloro-5-(2-{2-[(1H-imidazol-2-ylmethyl)-amino]-1,1-dimethyl-ethyl}-5-pyridin-4-yl-1H-imidazol-4-yl)-phenol | CH₂—(1H-imidazol-2-yl) | 1H-Imidazole-2-carbaldehyde | 423/425 |
| 30 | 2-Chloro-5-{2-[1,1-dimethyl-2-(4-trifluoromethoxy-benzylamino)-ethyl]-5-pyridin-4-yl-1H-imidazol-4-yl}-phenol | CH₂—(4-trifluoromethoxyphenyl) | 4-Trifluoromethoxy-benzaldehyde | 517/519 |
| 31 | 2-Chloro-5-(2-{2-[1-(2-methoxy-ethyl)-piperidin-4-ylamino]-1,1-dimethyl-ethyl}-5-pyridin-4-yl-1H-imidazol-4-yl)-phenol | 1-(2-methoxyethyl)-piperidin-4-yl | 1-(2-Methoxy-ethyl)-piperidin-4-one (J. L. Hughes et al, J. Med. Chem., 1971, 14, 894) | 484/486 |
| 32 | 2-Chloro-5-[2-(2-{[1-(2-methoxy-ethyl)-piperidin-4-ylmethyl]-amino}-1,1-dimethyl-ethyl)-5-pyridin-4-yl-1H-imidazol-4-yl]-phenol | CH₂—[1-(2-methoxyethyl)-piperidin-4-yl] | 1-(2-Methoxy-ethyl)-piperidine-4-carbaldehyde (Reagent A) | 498/500 |
| 33 | 2-Chloro-5-{2-[2-(2-methoxy-ethylamino)-1,1-dimethyl-ethyl]-5-pyridin-4-yl-1H-imidazol-4-yl}-phenol | (CH₂)₂OMe | Methoxyacetaldehyde | 401/403 |
| 34 | 2-Chloro-5-{2-[2-(5-hydroxy-pentylamino)-1,1-dimethyl-ethyl]-5-pyridin-4-yl-1H-imidazol-4-yl}-phenol | (CH₂)₅OH | 5-Hydroxy-pentanal | 429/431 |

Example 35

2-Chloro-5-[2-(1,1-dimethyl-2-morpholin-4-yl-ethyl)-5-pyridin-4-yl-1H-imidazol-4-yl]-phenol

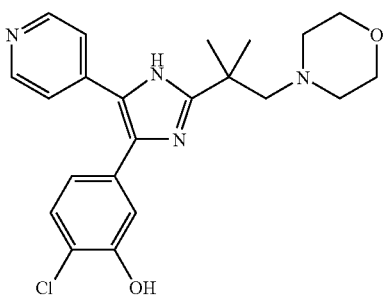

Step 1. 2-[4-(4-Chloro-3-methoxy-phenyl)-5-pyridin-4-yl-1H-imidazol-2-yl]-2-methyl-propionic acid methyl ester The title compound (5.1 g, 36%) was prepared from the product of Example 1 Step 3 and 2,2-dimethyl-3-oxo-propionic acid methyl ester (H. Kim et al, *Synth. Commun.*, 1997, 27, 2505) using the method described in Example 1 Step 4; MS(ES+) m/e 386/388 [M+H]+.

Step 2. 2-[4-(4-Chloro-3-hydroxy-phenyl)-5-pyridin-4-1yl-1H-imidazol-2-yl]-2-methyl-propionic acid A solution of the product of Step 1 (5.0 g, 13.0 mmol) in dichloromethane (200 ml) was cooled to 0° C. and treated with boron tribromide (1M solution in dichloromethane, 65 ml). The solution was allowed to warm to room temperature and stirred for 16 hours. Water (30 ml) was added and the mixture heated to reflux for 30 min. The reaction was concentrated in vacuo to remove the dichloromethane, washed with ethyl acetate and then filtered through celite. The pH of the aqueous phase was adjusted to 11 by the addition of aqueous sodium hydroxide solution and the mixture heated to 50° C. for 2 hours. The reaction mixture was washed with ethyl acetate and the aqueous phase adjusted to pH 4.5 whereby the product precipitated. The precipitate was collected by collected by filtration, washed with water and diethyl ether and dried over phosphorus pentoxide to give the title compound (2.36 g, 51%); MS(ES+) m/e 358/360 [M+H]+.

Step 3. 2-[4-(4-Chloro-3-hydroxy-phenyl)-5-pyridin-4-yl-1H-imidazol-2-yl]-2-methyl-propionyl chloride Oxalyl chloride (2.5 ml, 28.6 mmol) was added to a suspension of the product of Step 2 (2.1 g, 5.87 mmol) in dichloromethane (100 ml) containing DMF (0.1 ml). The mixture was heated to reflux for 20 hours and then concentrated in vacuo. The residue was re-suspended in dichloromethane and concentrated in vacuo to yield the title compound which was used directly in the following step.

Step 4. 2-[4-(4-Chloro-3-hydroxy-phenyl)-5-pyridin-4-yl-1H-imidazol-2-yl]-N-methoxy-N-methyl-isobutyramide N,O-Dimethylhydroxylamine hydrochloride (630 mg, 6.4 mmol) was added to a suspension of the product of Step 3 in acetonitrile (50 ml). The mixture was cooled to 0° C. and treated with a solution of pyridine (5 ml) in acetonitrile (5 ml). The reaction was stirred at room temperature for 16 hours and then concentrated in vacuo. The residue was redissolved in chloroform, washed with aqueous sodium carbonate solution, dried over magnesium sulphate, filtered and concentrated. The product was purified by silica gel chromatography eluting with chloroform/methanol/0.880 ammonia solution (8:2:0.2) to give the title compound (1.25 g, 53%); MS(ES+) m/e 401/403 [M+H]+.

Step 5. 2-[4-(4-Chloro-3-hydroxy-phenyl)-5-pyridin-4-yl-1H-imidazol-2-yl]-2-methyl-propionaldehyde Diisobutylaluminum hydride (12 ml, 1M solution in THF, 12.0 mmol) was added to a solution of the product of Step 4 (1.21 g, 3.0 mmol) in THF (60 ml) at −60° C. The mixture was allowed to warm to room temperature over 2 hours and then cooled to −60° C. before pouring into 2M hydrochloric acid (10 ml) at −20° C. with vigorous stirring. The mixture was warmed to room temperature and then basified with aqueous sodium hydrogen carbonate solution. The product was extracted into chloroform (X 3), dried over magnesium sulphate and concentrated in vacuo to yield the title compound (525 mg, 51%); MS(ES+) m/e 342/344 [M+H]+.

Step 6. 2-Chloro-5-[2-(1,1-dimethyl-2-morpholin-4-yl-ethyl)-5-pyridin-4-yl-1H-imidazol-4-yl]-phenol A mixture of the product of the product of Step 5 (100 mg, 0.30 mmol), morpholine (0.05 ml, 0.57 mmol) and polymer bound trimethylammonium cyanoborohydride (150 mg, 0.6 mmol, 4 mmol/g) in methanol (8 ml) containing glacial acetic acid (0.05 ml) was stirred at room temperature for 24 hours. The reaction was then filtered, the filtrate concentrated in vacuo and the product purified by silica gel chromatography eluting with chloroform/methanol/0.880 ammonia solution (9:1:0.1) to yield the title compound (80 mg, 65%); MS(ES+) m/e 413/415 [M+H]+.

Examples 36–40

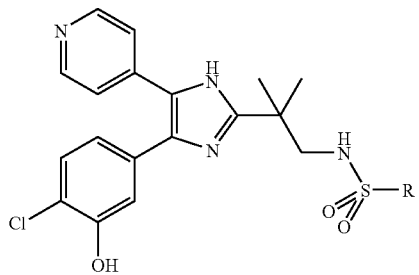

Examples 36–40 were prepared by the following general procedure.

A solution of the specified sulphonyl chloride (0.3 mmol) in dichloromethane (0.5 ml) was added to an ice-cooled solution of the product of Example 3 (100 mg, 0.29 mmol) and N,N-di-isopropylethylamine (0.09 mmol) in dichloromethane (2 ml) and N,N-dimethylformamide (0.2 ml). After stirring at room temperature for 1–24 hours the mixture was diluted with dichloromethane and water, and the pH adjusted to pH 6–7. The organic layer was then separated, washed with brine, dried over anhydrous magnesium sulfate, filtered and the filtrate concentrated in vacuo. The product was then purified by silica gel chromatography.

| Example No. | Name | R | Sulfonyl chloride | Mass spec MS(AP+) m/e[M + H] |
|---|---|---|---|---|
| 36 | N-{2-[4-(4-Chloro-3-hydroxy-phenyl)-5-pyridin-4-yl-1H-imidazol-2-yl]-2-methYlpropyl}-benzenesulfonamide | Ph | Benzenesulfonyl chloride | 483/485 |
| 37 | 4-{2-[4-(4-Chloro-3-hydroxy-phenyl)-5-pyridin-4-yl-1H-imidazol-2-yl]-2-methyl-propylsulfamoyl}-benzoic acid | | 4-Chlorosulfonyl-benzoic acid | 527/529 |
| 38 | 5-{2-[4-(4-Chloro-3-hydroxy-phenyl)-5-pyridin-4-yl-1H-imidazol-2-yl]-2-methyl-propylsulfamoyl}-2-hydroxy-benzoic acid | | 5-Chlorosulfonyl-2-hydroxy-benzoic acid | 543/545 |
| 39 | N-{2-[4-(4-Chloro-3-hydroxy-phenyl)-5-pyridin-4-yl-1H-imidazol-2-yl]-2-methyl-propyl}-4-cyano-benzenesulfonamide | | 4-Cyanobenzenesulfonyl chloride | 508/510 |
| 40 | N-{2-[4-(4-Chloro-3-hydroxy-phenyl)-5-pyridin-4-yl-1H-imidazol-2-yl]-2-methyl-propyl}-1-phenyl-methanesulfonamide | PhCH$_2$ | Phenylmethanesulfonyl chloride | 497/499 |

Example 41

4-Aminomethyl-N-{2-[4-(4-chloro-3-hydroxy-phenyl)-5-pyridin-4-yl-1H-imidazol-2-yl]-2-methyl-propyl}-benzenesulfonamide

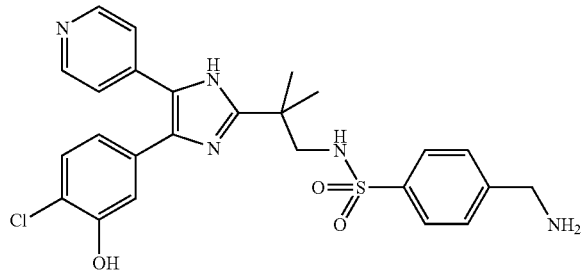

A solution of the product of Example 39 (70 mg, 0.14 mmol) and borane-methyl sulfide complex (0.080 ml, 0.84 mmol) in tetrahydrofuran (5 ml) was heated to reflux for 4 hours. After cooling to room temperature methanol (1 ml) was added and the mixture heated to reflux for a further 30 min. 2M hydrochloric acid (1 ml) was then added and the mixture again heated to reflux for 1 hour. The reaction mixture was then cooled to room temperature, the pH adjusted to pH 9 with saturated potassium carbonate solution and the mixture extracted with ethyl acetate. The combined extracts were dried over anhydrous magnesium sulfate, filtered, the solvent removed under reduced pressure and the residue purified by silica gel chromatography eluting with dichloromethane/methanol/0.880 ammonia solution (5:1:0.1) to give the title compound 35 mg (49%); MS(AP+) m/e 512/514 [M+H]+.

Example 42

2-(4-Methyl-piperazin-1-yl)-ethanesulfonic acid {2-[4-(4-chloro-3-hydroxy-phenyl)-5-pyridin-4-yl-1H-imidazol-2-yl]-2-methyl-propyl}-amide

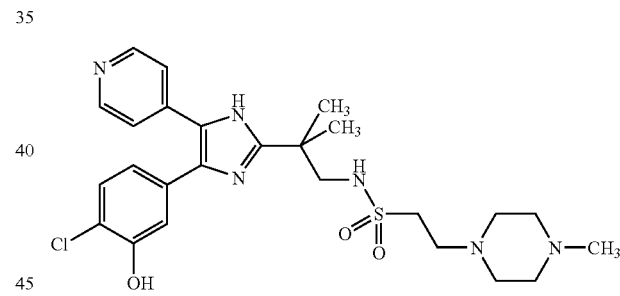

Step 1. Ethensulfonic acid {2-[4-(4-chloro-3-methoxy-phenyl)-5-pyridin-4-yl-1H-imidazol-2-yl]-2-methyl-propyl}-amide A solution of ethenesulfonyl chloride (J. Marchand-Brynaert et al., Tetrahedron 1966, 52, 5591) (230 mg, 1.8 mmol) in dichloromethane (10 ml) was cooled to −78° C. and treated with a solution of the product of Example 2 and triethylamine (0.4 ml, 3 mmol) in dichloromethane (10 ml). After 1 hour the reaction mixture was warmed to room temperature and the solution washed with saturated sodium hydrogen carbonate solution. The organic layer was separated, washed with water and brine, dried over anhydrous magnesium sulfate, filtered and the solvent evaporated to give the title compound (254 mg, 38%); MS(ES+) m/e 447/449 [M+H]+.

Step 2. 2-(4-Methyl-piperazin-1-yl)-ethanesulfonic acid {2-[4-(4-chloro-3-methoxy-phenyl)-5-pyridin-4-yl-1H-imidazol-2-yl]-2-methyl-propyl}-amide A solution of the produce of Step 1 (110 mg, 0.25 mmol) and N-methylpiperazine (50 mg, 0.5 mmol) in dichloromethane (5 ml) was stirred at room temperature for 72 hours. The solvent was evaporated and the residue was purified by silica gel chromatography to give the title compound (98 mg, 72%); MS(ES+) m/e 547/549 [M+H]+.

Step 3. 2-(4-Methyl-piperazin-1-yl)-ethanesulfonic acid {2-[4-(4-chloro-3-hydroxy-phenyl)-5-pyridin-4-yl-1H-imidazol-2-yl]-2-methyl-propyl}-amide The title compound was prepared from the product of Step 2 using the method described in Example 3 and the product purified by silica gel chromatography; MS(ES+) m/e 533/535 [M+H]+.

Example 43

2-Morpholin-4-yl-ethanesulfonic acid {2-[4-(4-chloro-3-hydroxy-phenyl)-5-pyridin-4-yl-1H-imidazol-2-yl]-2-methyl-propyl}-amide

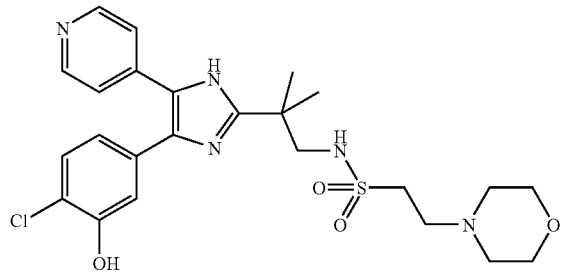

The title compound was prepared from morpholine and the product of Example 42 Step 1 using the method described in Example 42 Steps 2 and 2; MS(ES+) m/e 520/522 [M+H]+.

Examples 44–48

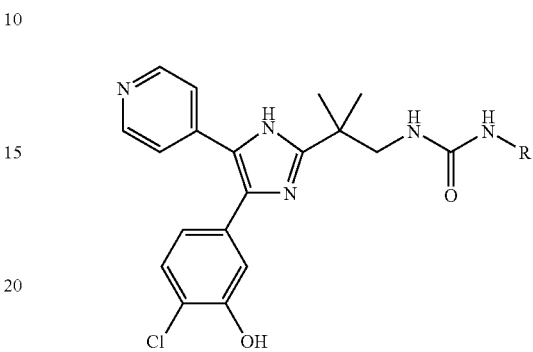

Examples 44–48 were prepared by the following general procedure. The specified amine (0.24 mmol) and triphosgene (33 mg, 0.11 mmol) were added to a suspension of polymer bound diisopropylethylamine (200 mg) in dichloromethane (3 ml). After stirring for 30 min at room temperature the mixture was treated with the product of Example 3 (100 mg, 0.30 mmol). the reaction was then stirred for 3 hours, filtered, the filtrate concentrated in vacuo and the product purified by silica gel chromatography.

| Example No. | Name | R | Amine | Mass spec MS(AP+) m/e[M + H]+ |
|---|---|---|---|---|
| 44 | 1-{2-[4-(4-Chloro-3-hydroxy-phenyl)-5-pyridin-4-yl-1H-imidazol-2-yl]-2-methyl-propyl}-3-phenyl-urea | Ph | Aniline | 462/464 |
| 45 | 1-{2-[4-(4-Chloro-3-hydroxy-phenyl)-5-pyridin-4-yl-1H-imidazol-2-yl]-2-methyl-propyl}-3-(3-morpholin-4-yl-propyl)-urea | (CH$_2$)$_3$-morpholine | 4-(3-Aminopropyl) morpholine | 513/515 |
| 46 | 1-{2-[4-(4-Chloro-3-hydroxy-phenyl)-5-pyridin-4-yl-1H-imidazol-2-yl]-2-methyl-propyl}-3-[4-(2-dimethylamino-ethoxy)-phenyl]-urea | C$_6$H$_4$-OCH$_2$CH$_2$NMe$_2$ | 4-(2-Dimethylamino ethoxy)-phenylamine, (R. S. Shadbolt et al, J. Med Chem., 1971, 14, 836) | 549/551 |
| 47 | 1-{2-[4-(4-Chloro-3-hydroxy-phenyl)-5-pyridin-4-yl-1H-imidazol-2-yl]-2-methyl-propyl}-3-[4-methoxy-3-(4-methyl-piperazin-1-yl)-phenyl]-urea | 4-methoxy-3-(4-methylpiperazin-1-yl)phenyl | 4-Methoxy-3-(4-methyl-piperazin-1-yl) phenylamine, (J. W. Clitherow et al, J. Med Chem., 1994, 37, 2253) | 590/592 |

-continued

| Example No. | Name | R | Amine | Mass spec MS(AP+) m/e[M + H]+ |
|---|---|---|---|---|
| 48 | 1-{2-[4-(4-Chloro-3-hydroxy-phenyl)-5-pyridin-4-yl-1H-imidazol-2-yl]-2-methyl-propyl}-3-[3-methoxy-4-(2-morpholin-4-yl-ethoxy)-phenyl]-urea | (OMe, O-CH2CH2-morpholine phenyl) | 3-Methoxy-4-(2-morpholin-4-yl-ethoxy)-phenylamine (Reagent B) | 621/643 |

Example 49

4-(2-Methoxy-ethyl)-piperazine-1-carboxylic acid {2-[4-(4-chloro-3-hydroxy-phenyl)-5-pyridin-4-yl-1H-imidazol-2-yl]-2-methyl-propyl}-amide

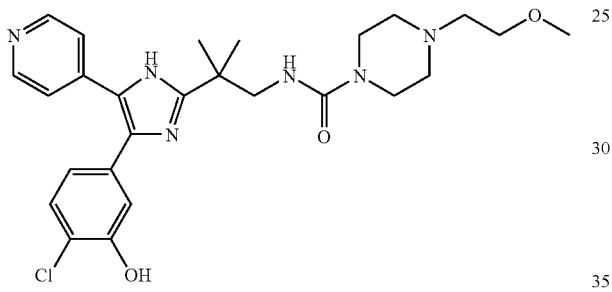

Step 1. 4-(2-Methoxy-ethyl)-piperazine-1-carbonyl chloride

A solution of 1-(2-methoxy-ethyl)-piperazine (100 mg, 0.69 mmol) and triethylamine (0.1 ml, 0.71 mmol) in dichloromethane (5 ml) was cooled to 0° C. and treated with a solution of trichloromethyl chloroformate (0.05 ml, 0.41 mmol) in dichloromethane (5 ml). The mixture was allowed to warm to room temperature, stirred for a further 1 hour then concentrated in vacuo. The crude product used without purification in the following reaction.

Step 2. 4-(2-Methoxy-ethyl)-piperazine-1-carboxylic acid {2-[4-(4-chloro-3-hydroxy-phenyl)-5-pyridin-4-yl-1H-imidazol-2-yl]-2-methyl-propyl}-amide To a solution of the product of Example 3 (240 mg, 0.70 mmol), triethylamine (0.2 ml, 1.43 mmol) and DMAP (5 mg) in dichloromethane (3 ml) was added a solution of the product of Step 1 in dichloromethane (5 ml). The reaction was heated to 80° C. for 16 hours, concentrated in vacuo, and the product purified by silica gel chromatography eluting with chloroform/methanol/0.880 ammonia solution (9:1:0.1) to yield the title compound (188 mg, 53%); MS(ES+) m/e 513/515 [M+H]+.

Example 50

5-[2-(2-Amino-1,1-dimethyl-ethyl)-5-pyridin-4-yl-1H-imidazol-4-yl]-2-bromo-phenol

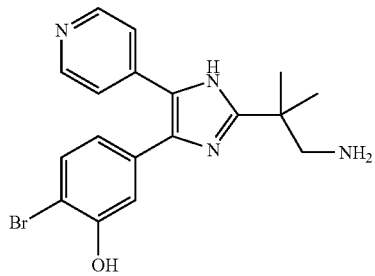

The title compound was prepared 4-bromo-3-methoxy-benzoic acid (G. M. Iskander, *J. Chem. Soc. Perkin Trans* 1.; 1973, 2202) using the methods described in Example 1 Steps 1–4, followed by Example 2 and Example 3; MS(ES+) m/e 387/389 [M+H]+.

Example 51

N-{2-[4-(4-Bromo-3-hydroxy-phenyl)-5-pyridin-4-yl-1H-imidazol-2-yl]-2-methyl-propyl}-methane-sulfonamide

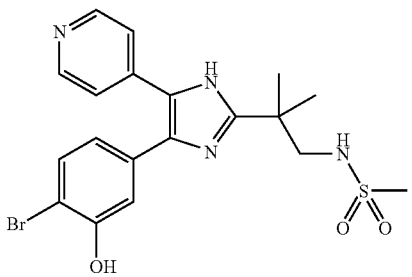

The title compound was prepared from the product of Example 50 using the method described in Example 11; MS(ES+) m/e 465/467 [M+H]+.

Example 52

2-Chloro-5-[2-(1,1-dimethyl-2-methylamino-ethyl)-5-pyridin-4-yl-1H-imidazol-4-yl]-phenol

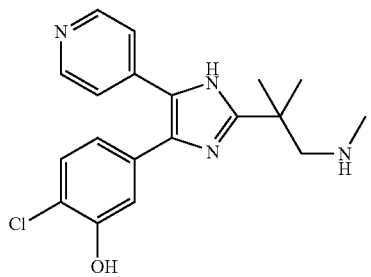

Step 1. (3-Hydroxy-2,2-dimethyl-propyl)-methyl-carbamic acid tert-butyl ester

A solution of 2,2-dimethyl-3-methylamino-propan-1-ol (A. G. Anderson, *J. Org. Chem.*, 1968, 33, 2123) (880 mg, 7.5 mmol) in tetrahydrofuran (30 ml) cooled in an ice bath was treated with a solution of di-tert-butyl dicarbonate (1.64 g, 7.5 mmol) in tetrahydrofuran (5 ml). After stirring at room temperature for 18 hours the solvent was removed under reduced pressure giving the title compound: MS(ES+) m/e 218 [M+H]+.

Step 2. (2,2-Dimethyl-3-oxo-propyl)-methyl-carbamic acid tert-butyl ester

A mixture of the product from Step 1 (1.62 g, 7.5 mmol), pyridinium chlorochromate (3.23 g, 15 mmol) and 4 A molecular sieves (10 g) in dichloromethane (50 ml) was stirred at room temperature for 5 hours. The reaction mixture was then poured onto a silica gel column, which was eluted with dichloromethane, to give the title compound, as an oil, which was used directly in the next reaction; $^1$H NMR (CDCl$_3$) 9.6 (1H, broad s), 3.35 (2H, s), 2.85 (3H, broad s), 1.44 (9H, s) and 1.07 (6H, s).

Step 3. {2-[4-(4-Chloro-3-methoxy-phenyl)-5-pyridin-4-yl-1H-imidazol-2-yl]-2-methyl-propyl}-methyl-carbamic acid tert-butyl ester The title compound was prepared from the product of Step 2 and the product of Example 1, Step 3 using the method described in Example 1 Step 4; MS(ES+) m/e 471/473 [M+H]+.

Step 4. 2-Chloro-5-[2-(1,1-dimethyl-2-methylamino-ethyl)-5-pyridin-4-yl-1H-imidazol-4-yl]-phenol The title compound was prepared from the product of Step 3 using the methods described in Example 2 followed by Example 3; MS(AP+) m/e 357/359 [M+H]+.

Examples 53–58

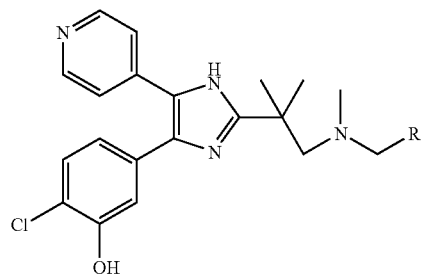

Examples 53–58 were prepared by the following general method. A mixture of the product of Example 52 (100 mg, 0.29 mmol), the specified aldehyde (0.32 mmol) and polymer bound trimethylammonium cyanoborohydride (125 mg, 0.5 mmol, 4 mmol/g) in methanol (3 ml) containing glacial acetic acid (0.05 ml) was stirred at room temperature for 24 hours. The reaction was then filtered, the filtrate concentrated in vacuo and the product purified by silica gel chromatography.

| Example No. | Name | R | Aldehyde | Mass spec MS(AP+) m/e[M + H]+ |
|---|---|---|---|---|
| 53 | 2-Chloro-5-{[(furan-3-ylmethyl-methyl-amino)-dimethyl-ethyl]-pyridin-4-yl-1H-imidazol-4-yl}-phenol | furan-3-yl-CH$_2$ | Furan-3-carbaldehyde | 437/439 |
| 54 | 2-Chloro-5-{[dimethyl-(methyl-pentyl-amino)ethyl]-pyridin-4-yl-1H-imidazol-4-yl}-phenol | C$_5$H$_{11}$ | Pentanal | 427/429 |
| 55 | 2-Chloro-5-[({[1-(2-methoxy-ethyl)-piperidin-4-yl]-methyl-amino}-dimethyl-ethyl)-pyridin-4-yl-1H-imidazol-4-yl]-phenol | 1-(2-methoxyethyl)piperidin-4-yl | 1-(2-Methoxyethyl)-piperidin-4-one (J. L. Hughes et al, J. Med. Chem., 1971, 14, 894) | 498/500 |
| 56 | 2-Chloro-5-[({[1-(2-methoxy-ethyl)-piperidin-4-ylmethyl]-methyl-amino}-dimethyl-ethyl)-pyridin-4-yl-1H-imidazol-4-yl]-phenol | 1-(2-methoxyethyl)piperidin-4-ylmethyl | 1-(2-Methoxyethyl)-piperidine-4-carbaldehyde (Reagent A) | 512/514 |

| Example No. | Name | R | Aldehyde | Mass spec MS(AP+) m/e[M + H]+ |
|---|---|---|---|---|
| 57 | 2-Chloro-5-({[(2-methoxy-ethyl)-methyl-amino]-dimethyl-ethyl}-pyridin-4-yl-1H-imidazol-4-yl)-phenol | $CH_2CH_2OMe$ | Methoxyacetaldehyde | 415/417 |
| 58 | 2-Chloro-5-{2-[2-benzylmethyl-methyl-amino)-1,1-dimethyl-ethyl]-pyridin-4-yl-1H-imidazol-4-yl}-phenol | $PhCH_2$ | Benzaldehyde | 447/449 |

Example 59

2-Chloro-5-({[(2-hydroxy-ethyl)-methyl-amino]-dimethyl-ethyl}-pyridin-4-yl-1H-imidazol-4-yl)-phenol trihydrochloride

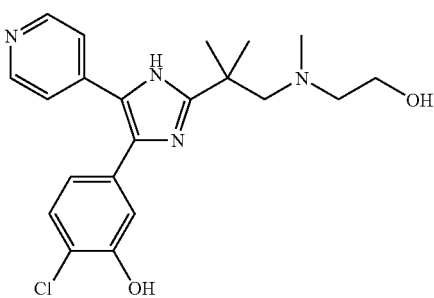

Step 1. 2-Chloro-5-[({[2-tert-Butyl-dimethyl-silanyloxy)-ethyl]-methyl-amino}-dimethyl-ethyl)-pyridin-4-yl-1H-imidazol-4-yl]-phenol The title compound (190 mg, 66%) was prepared from the product of Example 52 and tert-butyldimethylsilyloxyacetaldehyde using the general reductive alkylation method described for Examples 53–58; MS(ES+) m/e 515/517 [M+H]+.

Step 2. 2-Chloro-5-({[(2-hydroxy-ethyl)-methyl-amino]-dimethyl-ethyl}-pyridin-4-yl-1H-imidazol-4-yl)-phenol trihydrochloride A solution of the product of Step 1 (185 mg, 0.36 mmol) in methanol (3 ml) was treated with a 1M solution of HCl in diethyl ether (2 ml) and the mixture stirred for 2 h. The reaction was concentrated in vacuo and the product triturated with dichloromethane and ethyl acetate to yield the title compound (155 mg, 85%); MS(ES+) m/e 401/403 [M+H]+.

Example 60

4-(2-Methoxy-ethyl)-piperazine-1-carboxylic acid {2-[4-(4-chloro-3-hydroxy-phenyl)-5-pyridin-4-yl-1H-imidazol-2-yl]-2-methyl-propyl}-methyl-amide

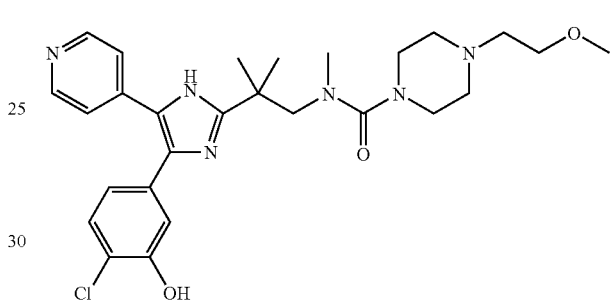

The title compound (170 mg, 41%) was prepared from the product of Example 52 and the product of Example 49 Step 1 using the method described in Example 49 Step 2; MS(ES+) m/e 527/529 [M+H]+.

Example 61

5-[2-(1-Aminomethyl-cyclohexyl)-5-pyridin-4-yl-1H-imidazol-4-yl]-2-chloro-phenol

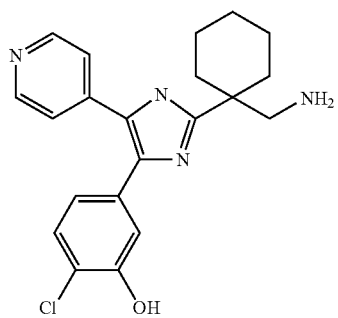

Step 1. {1-[4-(4-Chloro-3-methoxy-phenyl)-5-pyridin-4-yl-1H-imidazol-2-yl]-cyclohexylmethyl}-carbamic acid tert-butyl ester The title compound (1.08 g, 23%) was prepared from the product of Example 1 Step 3 and (1-formyl-cyclohexylmethyl)-carbamic acid tert-butyl ester (D. L. Varie et al, Bioorg. and Med. Chem. Lett., 1999, 9, 369) using the method described in Example 1 Step 4; MS(ES+) m/e 497/499 [M+H]+.

Step 2. {1-[4-(4-Chloro-3-methoxy-phenyl)-5-pyridin-4-yl-1H-imidazol-2-yl]-cyclohexyl}-methylamine The title compound was prepared from the product of Step 1 using the method described in Example 2; MS(ES+) m/e 397/399 [M+H]+.

Step 3. 5-[2-(1-Aminomethyl-cyclohexyl)-5-pyridin-4-yl-1H-imidazol-4-yl]-2-chloro-phenol The title compound was prepared from the product of Step 2 using the method described in Example 3; MS(ES+) m/e 383/385 [M+H]+.

Example 62

2-Chloro-5-(2-{1-[4-chloro-benzylamino)-methyl]-cyclohexyl}-5-pyridin-4-yl-1H-imidazol-4-yl)-phenol

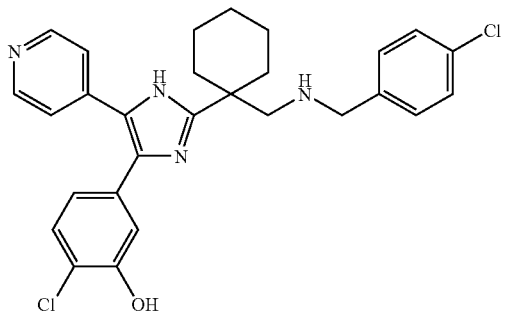

The title compound was prepared from the product of Example 62 and 4-chloro-benzaldehyde using the general reductive alkylation method described for Examples 12–34; MS(ES+) m/e 507/509 [M+H]+.

Example 63

5-[2-(1-Amino-1-methyl-ethyl)-5-pyridin-4-yl-1H-imidazol-4-yl]-2-chloro-phenol

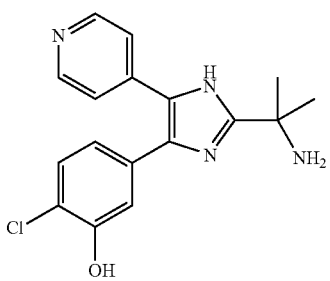

The title compound was prepared from the product of Example 1, Step 3 and 2-tert-butoxycarbonylamino-2-methylpropanal (T. Seki et al., Chem. Pharm. Bull.; 1996, 44, 2061) using the methods described in Example 1 Step 4, followed by those of Example 2 and Example 3; MS(ES+) m/e 329/331 [M+H]+.

Example 64

N-{1-[4-(4-Chloro-3-hydroxy-phenyl)-5-pyridin-4-yl-1H-imidazol-2-yl]-1-methyl-ethyl}-methane-sulfonamide

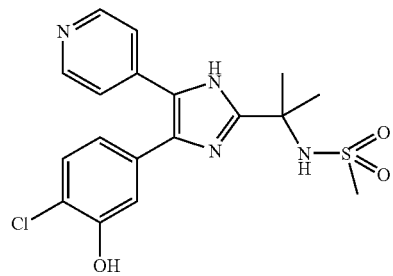

The title compound was prepared from product of Example 63 using the methods described in Example 4 followed by Example 3. The product was purified by silica gel chromatography; MS(ES+) m/e 407/409 [M+H]+.

Examples 65–78

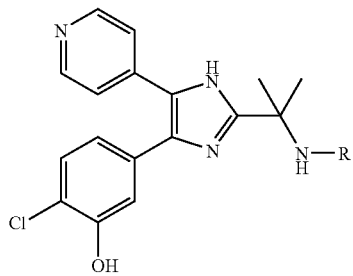

Examples 65–78 were prepared by the following general method. A mixture of the product of Example 63 (100 mg, 0.29 mmol), the specified aldehyde (0.32 mmol) and polymer bound trimethylammonium cyanoborohydride (125 mg, 0.5 mmol, 4 mmol/g) in methanol (3 ml) containing glacial acetic acid (0.05 ml) was stirred at room temperature for 24 hours. The reaction was then filtered, the filtrate concentrated in vacuo and the product purified by silica gel chromatography.

| Example No. | Name | R | Aldehyde | Mass spec MS(AP+) m/e[M + H]+ |
|---|---|---|---|---|
| 65 | 2-Chloro-5-{2-[1-(4-methoxy-benzylamino)-1-methyl-ethyl]-5-pyridin-4-yl-1H-imidazol-4-yl}-phenol | 4-methoxybenzyl group | 4-Methoxybenzaldehyde | 449/451 |
| 66 | 2-Chloro-5-{2-[1-(3-methoxy-benzylamino)-1-methyl-ethyl]-5-pyridin-4-yl-1H-imidazol-4-yl}-phenol | 3-methoxybenzyl group | 3-Methoxybenzaldehyde | 449/451 |
| 67 | 2-Chloro-5-{2-[1-(3,4-dichloro-benzylamino)-1-methyl-ethyl]-5-pyridin-4-yl-1H-imidazol-4-yl}-phenol | 3,4-dichlorobenzyl group | 3,4-Dichlorobenzaldehyde | 488/490 492/494 |
| 68 | 2-Chloro-5-}2-[1-(4-methanesulfonyl-benzylamino)-1-methyl-ethyl]-5-pyridin-4-yl-1H-imidazol-4-yl}-phenol | 4-methanesulfonylbenzyl group | 4-Methanesulfonyl benzaldehyde | 497/499 |
| 69 | 2-Chloro-5-{2-[1-(4-trifluoromethyl-benzylamino)-1-methyl-ethyl]-5-pyridin-4-yl-1H-imidazol-4-yl}-phenol | 4-trifluoromethylbenzyl group | 4-Trifluoromethyl benzaldehyde | 487/489 |
| 70 | 2-Chloro-5-{2-[1-methyl-1-(4-pyrrolidin-1-yl-benzylamino)-1-methyl-ethyl]-5-pyridin-4-yl-1H-imidazol-4-yl}-phenol | 4-pyrrolidin-1-yl-benzyl group | 4-Pyrrolidin-1-yl-benzaldehyde | 488/490 |
| 71 | N-[4-({1-[4-(4-Chloro-3-hydroxy-phenyl)-5-pyridin-4-yl-1H-imidazol-2-yl]-1-methyl-ethylamino}-methyl)-phenyl]-acetamide | 4-acetamidobenzyl group | N-(4-formyl-phenyl)-acetamide | 476/478 |
| 72 | 2-Chloro-5-(2-{1-[(furan-3-ylmethyl)-amino]-1-methyl-ethyl}-5-pyridin-4-yl-1H-imidazol-4-yl)-phenol | furan-3-ylmethyl group | Furan-3-carbaldehyde | 409/411 |
| 73 | 2-Chloro-5-(2-{1-methyl-1-[(pyridin-3-ylmethyl)-amino]-ethyl}-5-pyridin-4-yl-1H-imidazol-4-yl)-phenol | pyridin-3-ylmethyl group | Pyridine-3-carbaldehyde | 420/422 |
| 74 | 2-Chloro-5-(2-1-[(1H-imidazol-2-ylmethyl)amino]-1-methyl-ethyl}-5-pyridin-4-yl-1H-imidazol-4-yl)-phenol | 1H-imidazol-2-ylmethyl group | 1H-imidazole-2-carbaldehyde | 409/411 |
| 75 | 2-Chloro-5-(2-{1-methyl-1-[(thiazol-2-ylmethyl)-amino]-ethyl}-5-pyridin-4-yl-1H-imidazol-4-yl)-phenol | thiazol-2-ylmethyl group | Thiazole-2-carbaldehyde | 426/428 |

-continued

| Example No. | Name | R | Aldehyde | Mass spec MS(AP+) m/e[M + H]+ |
|---|---|---|---|---|
| 76 | 2-Chloro-5-(2-{1-methyl-1-[(thiophen-2-ylmethyl)-amino]-ethyl}-5-pyridin-4-yl-1H-imidazol-4-yl)-phenol | CH2—[thiophene] | Thiophene-2-carbaldehyde | 425/427 |
| 77 | 2-Chloro-5-{2-[1-methyl-1-(4-trifluoromethoxy-benzylamino)-ethyl]-5-pyridin-4-yl-1H-imidazol-4-yl}-phenol | CH2—[phenyl]-OCF3 | 4-Trifluoromethoxy-benzaldehyde | 503/505 |
| 78 | 2-Chloro-5-[2-(1-{[1-(2-methoxy-ethyl)-piperidin-4-ylmethyl]-amino}-1-methyl-ethyl)-5-pyridin-4-yl-1H-imidazol-4-yl]-phenol | CH2—[piperidine]-NCH2CH2OMe | 1-(2-Mmethoxyethyl)-piperidine-4-carbaldehyde (Reagent A) | 484/466 |

Examples 79–82

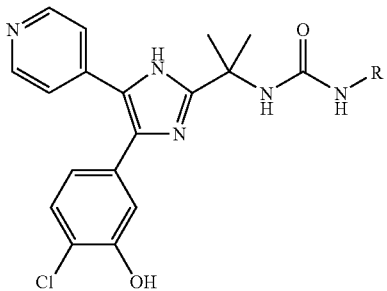

Examples 79–82 were prepared by the following general method. The specified amine (0.24 mmol) and triphosgene (33 mg, 0.11 mmol) were added to a suspension of polymer bound diisopropylethylamine (200 mg) in dichloromethane (3 ml). After stirring for 30 min at room temperature the mixture was treated with the product of Example 63 (100 mg, 0.30 mmol). The reaction was then stirred for 3 hours, filtered, the filtrate concentrated in vacuo and the product purified by silica gel chromatography.

| Example No. | Name | R | Amine | Mass spec MS(AP+) m/e[+ H]+ |
|---|---|---|---|---|
| 79 | 1-{1-[4-(4-Chloro-3-hydroxy-phenyl)-5-pyridin-4-yl-1H-imidazol-2-yl]-1-methyl-ethyl}-3-phenyl-urea | Ph | Aniline | 448/450 |
| 80 | 1-{1-[4-(4-Chloro-3-hydroxy-phenyl)-5-pyridin-4-yl-1H-imidazol-2-yl]-1-methyl-ethyl}-3-[4-(2-dimethylamino-ethoxy)-phenyl]-urea | ←[phenyl]-OCH2CH2NMe2 | 4-(2-Dimethylamino ethoxy)-phenylamine, (R. S. Shadbolt et at, J. Med. Chem., 1971, 14, 836) | 535/537 |
| 81 | 1-{1-[4-(4-Chloro-3-hydroxy-phenyl)-5-pyridin-4-yl-1H-imidazol-2-yl]-1-methyl-ethyl}-3-[4-methoxy-3-(4-methyl piperazin-1-yl)-phenyl]-urea | ←[phenyl with OMe and N-methylpiperazine] | 4-Methoxy-3-(4-methyl-piperazin-1-yl)-phenylamine (J. W. Clitherow et at, J. Med. Chem., 1994, 37, 2253) | 576/578 |

| Example No. | Name | R | Amine | Mass spec MS(AP+) m/e[+ H]+ |
|---|---|---|---|---|
| 82 | 1-{1-[4-(4-Chloro-3-hydroxy-phenyl)-5-pyridin-4-yl-1H-imidazol-2-yl]-1-methyl-ethyl}-3-[3-methoxy-4-(2-morpholin-4-yl-ethoxy)-phenyl]-urea | 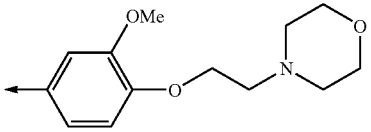 | 3-Methoxy-4-(2-morpholin-4-yl-ethoxy)-phenylamine (Reagent B) | 607/609 |

Example 83

5-[2-(2-Amino-1,1-dimethyl-ethyl)-5-(2-amino-pyrimidin-4-yl)-1H-imidazol-4-yl]-2-chloro-phenol

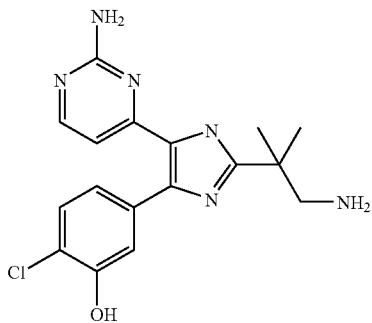

Step 1. 1-(4-Chloro-3-methoxy-phenyl)-2-(2-methylsulfanyl-pyrimidn-4-yl)-ethanone The title compound (0.650 g, 48%) was prepared from product of Example 1 Step 1 and 4-methyl-2-methylsulfanyl-pyrimidine using the method described in Example 1 Step 2; MS(AP+) m/e 309/311 [M+H]+.

Step 2. 1-(4-Chloro-3-methoxy-phenyl)-2-(2-methylsulfanyl-pyrimidin-4-yl)-ethane-1,2-dione 2-oxime Sodium nitrite (0.290 g, 4.2 mmol) was added portionwise to a suspension of the product from Step 1 (0.650 g, 2.1 mmol) in 3M HCl (10 ml) at 0° C. After 30 min the suspension was warmed to room temperature and stirred for 18 hours. The suspension was then adjusted to pH 8 with 2M aqueous sodium hydroxide solution and the solid filtered off and dried in vacuo to give the title compound (0.650 g, 92%) as a pale yellow solid; MS(AP−) m/e 336/338 [M−H]−.

Step 3. {2-[4-(4-Chloro-3-methoxy-phenyl)-1-hydroxy-5-(2-methylsulfanyl-pyrimidin-4-yl)-1H-imidazol-2-yl]-2-methyl-propyl}-carbamic acid tert-butyl ester The product of Step 2 (0.6 g, 1.78 mmol), (2,2-dimethyl-3-oxo-propyl)-carbamic acid tert-butyl ester (0.715 g, 3.56 mmol) and ammonium acetate (1.37 g, 17.8 mmol) were dissolved in acetic acid (10 ml) and heated to reflux for 3 hours. After cooling to room temperature, the reaction was poured into a slurry of ammonium hydroxide and ice and then extracted with ethyl acetate. The organic extracts were then washed with water, dried over magnesium sulphate, filtered and concentrated in vacuo. The residue was then purified by silica gel chromatography eluting with ethyl acetate/hexane (1:1) to give the title compound as a yellow solid; MS(AP+) m/e 520/522 [M+H]+.

Step 4. {2-[4-(4-Chloro-3-methoxy-phenyl)-5-(2-methylsulfanyl-pyrimidin-4-yl)-1H-imidazol-2-yl]-2-methyl-propyl}-carbamic acid tert-butyl ester A stirred solution of the product of Step 3 (0.420 g, 0.81 mmol) in DMF (10 ml) at 100° C. was treated with triethylphosphite (2.68 g, 16.2 mmol). After stirring for 1 hour the mixture was then cooled, concentrated in vacuo and the residue chromatographed on silica gel eluting with dichloromethane/diethyl ether (9:1) to give the title compound as a colourless gum (0.40 g, 97%); MS(AP+) m/e 504/506 [M+H]+.

Step 5. {2-[4-(4-Chloro-3-methoxy-phenyl)-5-(2-methanesulfonyl-pyrimidin-4-yl)-1H-imidazol-2-yl]-2-methyl-propyl}-carbamic acid tert-butyl ester A suspension of the product of Step 4 (0.3 g, 0.6 mmol) in methanol (10 ml) was treated with Oxone (0.735 g, 1.2 mmol) in water (10 ml) and, after 3 hours, additional Oxone (0.367 g, 0.6 mmol) in water (5 ml). After a further 2 hours the mixture was filtered and the filtrate diluted with ethyl acetate. The organic layer was then separated, dried (magnesium sulphate), concentrated and the crude product used directly in the next step; MS(AP+) m/e 536/538 [M+H]+.

Step 6. {2-[5-(2-Amino-pyrimidin-4-yl)-4-(4-chloro-3-methoxy-phenyl)-1H-imidazol-2-yl]-2-methyl-propyl}-carbamic acid tert-butyl ester The crude product of Step 5 was dissolved in tetrahydrofuran (5 ml), treated with 0.880 ammonia solution (20 ml) and then heated at 100° C. in an autoclave. After 4 hours the reaction was cooled to room temperature, concentrated in vacuo and the residue chromatographed on silica gel eluting with dichloromethane/methanol/0.880 ammonia solution (19:1:0.1) to give the title compound (0.2 g, 70%, 2 steps) as a yellow solid; MS(AP+) m/e 573/575 [M+H]+.

Step 7. 4-[2-(2-Amino-1,1-dimethyl-ethyl)-5-(4-chloro-3-methoxy-phenyl)-3H-imidazol-4-yl]-pyrimidin-2-ylamine A solution of the product of Step 6 (0.200 g, 0.42 mmol) in dichloromethane (5 ml) containing trifluoroacetic acid (2 ml) was stirred at room temperature for 2 hours. The solution was concentrated at reduced pressure and the residue parti Step 8. 5-[2-(2-Amino-1,1-dimethyl-ethyl)-5-(2-amino-pyrimidin-4-yl)-1H-imidazol-4-yl]-2-chloro-phenol A solution of the product of Step 7 (0.100 g, 0.27 mmol) in dichloromethane (5 ml) was cooled to 5° C. and treated with boron tribromide (1.3 ml, 1.3 mmol, 1M in dichloromethane). The solution was then stirred at room temperature for 1 hour before additional boron tribromide (0.6 ml, 0.6 mmol) was added. After a further 1 hour, water (5 ml) was added and the reaction then heated to 50° C. for 1 hour. The mixture was then cooled and the solvent removed in vacuo and the residue redissolved in ethanol and treated with 0.880 ammonia (9:1) to give the title compound (0.035 g, 36%) as a yellow solid; MS(ES+) m/e 359/361 [M+H]+.

Examples 84–95

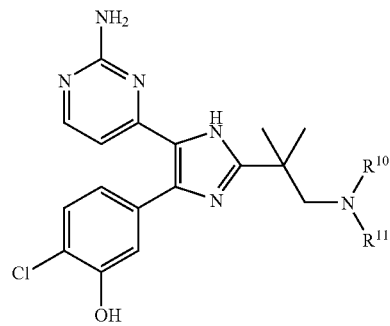

Examples 84–95 were prepared by the following general method. A mixture of the product of Example 83 (100 mg, 0.28 mmol), the specified aldehyde (0.31 mmol) and polymer bound trimethylammonium cyanoborohydride (125 mg, 0.5 mmol, 4 mmol/g) in methanol (3 ml) containing glacial acetic acid (0.05 ml) was stirred at room temperature for 24 hours. The reaction was then filtered, the filtrate concentrated in vacuo and the product purified by silica gel chromatography.

| Example No. | Name | $R^{10}$ | $R^{11}$ | Amine | Mass spec MS(ES+) m/e[M + H]+ |
|---|---|---|---|---|---|
| 84 | 5-{5-(2-Amino-pyrimidin-4-yl)-2-[2-(3,4-dichloro-benzylamino)-1,1-dimethyl-ethyl]-1H-imidazol-4-yl}-2-chloro-phenol | H | CH$_2$—(3,4-dichlorophenyl) | 3,4-Dichlorobenzaldehyde | 517/519/521/522 |
| 85 | 5-(5-(2-Amino-pyrimidin-4-yl)-2-{2-[2-(3,4-difluoro-phenoxy)-ethylamino]-1,1-dimethyl-ethyl}-1H-imidazol-4-yl)-2-chloro-phenol | H | CH$_2$CH$_2$O—(3,4-difluorophenyl) | (3,4-Difluorophenoxy)-acetaldehyde (Reagent C) | 515/517 |
| 86 | 5-[5-(2-Amino-pyrimidin-4-yl)-2-(1,1-dimethyl-2-piperidin-1-yl-ethyl)-1H-imidazol-4-yl]-2-chloro-phenol | —(CH$_2$)$_5$— | | Pentane-1,5-dial | 427/429 |
| 87 | 5-(5-(2-Amino-pyrimidin-4-yl)-2-{2-[2-(4-chloro-phenoxy)-ethylamino]-1,1-dimethyl-ethyl}-1H-imidazol-4-yl)-2-chloro-phenol | H | CH$_2$CH$_2$O—(4-chlorophenyl) | (4-Chlorophenoxy)-acetaldehyde (J. Sadet et al Bull. Soc. Chim. Fr., 1973, 6, 2016) | 513/515/517 |
| 88 | 5-(5-(2-Amino-pyrimidin-4-yl)-2-{1,1-dimethyl-2-[(thiophen-2-ylmethyl)-amino]-ethyl}-1H-imidazol-4-yl)-2-chlorophenol | H | CH$_2$—(4-OCF$_3$-phenyl) | 2-Thiophene-carboxaldehyde | 455/457 |
| 89 | 5-{5-(2-Amino-pyrimidin-4-yl)-2-[1,1-dimethyl-2-(4-trifluoromethyl-benzylamino)-ethyl]-1H-imidazol-4-yl}-2-chloro-phenol | H | CH$_2$—(4-OCF$_3$-phenyl) | 4-Trifluoromethoxy benzaldehyde | 517/519 |
| 90 | 5-{5-(2-Amino-pyrimidin-4-yl)-2-[2-(3-methoxy-benzylamino)-1,1-dimethyl-ethyl]-1H-imidazol-4-yl}-2-chloro-phenol | H | CH$_2$—(3-OMe-phenyl) | m-Anisaldehyde | 479/481 |

-continued

| Example No. | Name | R10 | R11 | Amine | Mass spec MS(ES+) m/e[M + H]+ |
|---|---|---|---|---|---|
| 91 | 5-{5-(2-Amino-pyrimidin-4-yl)-2-[2-(3,4-difluoro-benzylamino)-1,1-dimethyl-ethyl]-1H-imidazol-4-yl}-2-chloro-phenol | H | CH2-C6H3(F)(F) (3,4-difluorobenzyl) | 3,4-Difluorobenzaldehyde | 485/487 |
| 92 | 5-{5-(2-Amino-pyrimidin-4-yl)-2-[2-(3,5-dichloro-benzylamino)-1,1-dimethyl-ethyl]-1H-imidazol-4-yl}-2-chloro-phenol | H | CH2-C6H3(Cl)(Cl) (3,5-dichlorobenzyl) | 3,5-Dichlorobenzaldehyde | 517/519/ 521/523 |
| 93 | 5-{5-(2-Amino-pyrimidin-4-yl)-2-[2-(4-tert-butyl-benzylamino)-1,1-dimethyl-ethyl]-1H-imidazol-4-yl}-2-chloro-phenol | H | CH2-C6H4-tBu (4-tert-butylbenzyl) | 4-tert-Butyl-benzaldehyde | 505/507 |
| 94 | 5-(5-(2-Amino-pyrimidin-4-yl)-2-{1,1-dimethyl-2-[3-(3-trifluoromethyl-phenoxy)-benzylamino]-ethyl}-1H-imidazol-4-yl)-2-chloro-phenol | H | CH2-C6H4-O-C6H4-CF3 | 3-(3-Trifluoromethyl-phenoxy)-benzaldehyde | 609/611 |
| 95 | 5-{5-(2-Amino-pyrimidin-4-yl)-2-[1,1-dimethyl-2-(3-phenoxy-benzylamino)-ethyl]-1H-imidazol-4-yl}-2-chloro-phenol | H | CH2-C6H4-OPh | 3-Phenoxybenzaldehyde | 541/543 |

Reagents

Reagent A: 1-(2-Methoxy-ethyl)-piperidine-4-carbaldehyde

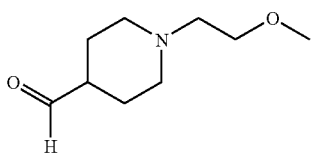

Step 1. 1-(2-Methoxyethyl)-piperidine-4-carboxylic acid ethyl ester

A solution of ethyl isonipecotate (26 g, 166 mmol) in ethanol (150 ml) was treated with potassium carbonate (41 g, 297 mmol) and 2-bromoethyl methyl ether (25 g, 179 mmol). The reaction mixture was heated to reflux for 24 hours, cooled and then filtered. The filtrate was concentrated in vacuo to yield the title compound (32.76 g, 92%); MS(ES+) m/e 216 [M+H]+.

Step 2. 1-(2-Methoxyethyl)-piperidine-4-carbaldehyde

Diisobutylaluminium hydride (10.2 ml, 1M solution in THF) was added to a solution of the product of Step 1 (2.0 g, 9.3 mmol) in toluene (40 ml) over a period of 1 hour at −78° C. The reaction was stirred at −78° C. for 1 hour and then quenched with methanol (5 ml) and aqueous ammonium acetate solution (5 ml). The mixture was stirred for 1 hour and then filtered through celite. The filtrate was concentrated in vacuo to yield the title compound (1.1 g, 69%); MS(ES+) m/e 172 [M+H]+.

Reagent B. 3-Methoxy-4-(2-morpholin-4-yl-ethoxy)-phenylamine

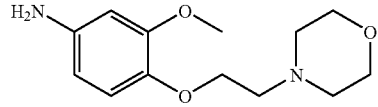

Step 1. 4-[2-(2-Methoxy-4-nitro-phenoxy)-ethyl]-morpholine

To a solution of (1-(2-hydroxyethyl)-morpholine) (1.94 ml, 16 mmol) in dimethylformamide was added sodium hydride [60% dispersion in oil] (544 mg, 16 mmol). After stirring at room temperature for 10 min, a solution of (1-chloro-2-methoxy-4-nitro-benzene) (3 g, 16 mmol) in dimethylformamide (10 ml) was added dropwise. The reaction mixture was left stirring at room temperature for 16 hours, concentrated, then the residue dissolved in ethyl acetate and washed with water. The organic phase was dried with magnesium sulphate, concentrated and the residue purified by column chromatography on silica gel to afford the title compound; MS(ES+) m/e 283 [M+H]+.

Step 2. 3-Methoxy-4-(2-morpholin-4-yl-ethoxy)-phenylamine

To a solution of the product of Step 1 (2.3 g, 8.6 mmol) in ethanol (100 ml) was added 10% palladium on charcoal (50 mg). The mixture was then stirred at room temperature under an atmosphere of hydrogen for 16 hours, filtered through celite and concentrated to give the title compound; MS(ES+) m/e 252 [M+H]+.

Reagent C: (3,4-Difluorophenoxy)-acetaldehyde

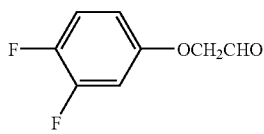

Step 1. 4-(2,2-Dimethoxyethoxy)-1,2-difluorobenzene

Bromoacetaldehyde dimethyl acetal (3.3 ml, 27.9 mmol) and potassium carbonate (6.5 g, 47.1 mmol) were added to a solution of 3,4-difluorophenol (3.0 g, 23.4 mmol) in DMF (65 ml). The mixture was heated to 120° C. for 4 hours, cooled to room temperature and then quenched with a solution of aqueous ammonium chloride. The product was extracted into ethyl acetate, washed with water and brine, dried over magnesium sulphate, filtered and concentrated in vacuo to yield the title compound (5.1 g, 97%); $^1$H NMR (CDCl$_3$) 3.45 (6H, s), 3.93 (2H, d, J 5.1 Hz), 4.67 (1H, t, J 5.1 Hz), 6.60 (1H, m), 6.74 (1H, m) and 7.03 (1H, m).

Step 2. (3,4-Difluorophenoxy)-acetaldehyde

A solution containing the product from Step 1 (5.1 g, 23.4 mmol), glacial acetic acid (4.5 ml) and concentrated sulphuric acid (2.7 ml) in water (50 ml) was heated at 100° C. for 5 hours. After cooling to room temperature, the product was extracted into diethyl ether. The organic extract was washed with aqueous sodium hydrogen carbonate solution, dried over magnesium sulphate, filtered an concentrated in vacuo. The product was purified by silica gel chromatography eluting with ethyl acetate:hexane (30:70) to yield the title compound (2.74 g, 68%); $^1$H NMR (CDCl$_3$) 4.52 (2H, s), 6.59 (1H, m), 6.83 (1H, m), 7.08 (1H, m) and 9.82 (1H, s).

BIOLOGICAL EXAMPLES

The activity of compounds of formula (I) as B-Raf inhibitors may be determined by the following in vitro assays:

Fluorescence anisotropy kinase binding assay

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×$K_i$) of a potent inhibitor the anisotropy of the unbound fluorescent ligand is measurable different from the bound value.

The concentration of kinase enzyme should preferably be ≧1×$K_f$. The concentration of fluorescent ligand required will depend on the instrumentation used, and the fluorescent and physicochemical properties. The concentration used must be lower than the concentration of kinase enzyme; and preferably less than half the kinase enzyme concentration. A typical protocol is:

All components dissolved in Buffer of composition 50 mM HEPES, pH 7.5, 1 mM CHAPS, 10 mM MgCL$_2$.
B-Raf Enzyme concentration: 1 nM
Fluorescent ligand concentration: 0.5 nM
Test compound concentration: 0.1 nM–100 uM
Components incubated in 10 ul final volume in LJL HE 384 type B black microtitre plate until equilibrium reached (Over 3 h, up to 30 h)
Fluorescence anisotropy read in LJL Acquest.

Definitions:
$K_i$=dissociation constant for inhibitor binding
$K_f$=dissociation constant for fluorescent ligand binding
The fluorescent ligand is the following compound:

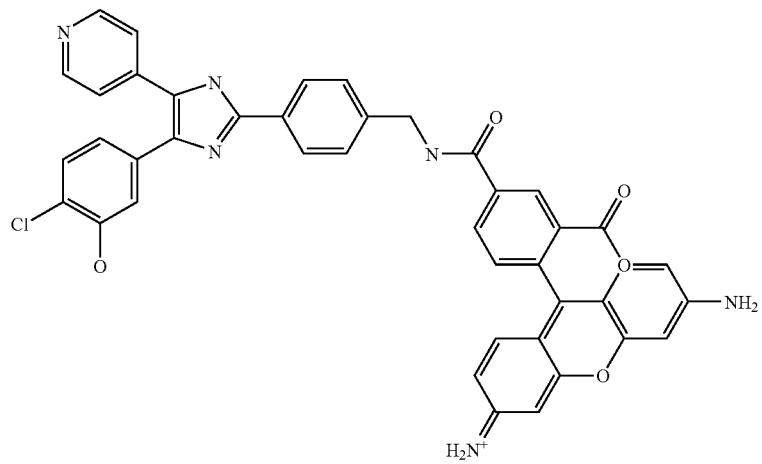

which is derived from 5-[2-(4-aminomethylphenyl)-5-pyridin-4-yl-1H-imidazol-4-yl]-2-chlorophenol and rhodamine green.

Raf Kinase Assay

Activity of human recombinant B-Raf protein was assessed in vitro by assay of the incorporation of radiolabelled phosphate to recombinant MAP kinase (MEK), a known physiologic substrate of B-Raf. Catalytically active human recombinant B-Raf protein was obtained by purification from sf9 insect cells infected with a human B-Raf recombinant baculovirus expression vector. To ensure that all substrate phosphorylation resulted from B-Raf activity, a catalytically inactive form of MEK was utilised. This protein was purified from bacterial cells expression mutant inactive MEK as a fusion protein with glutathione-S-transferase (GST-kdMEK).

Method: Standard assay conditions of B-Raf catalytic activity utilised 3 ug of GST-kdMEK, 10 uM ATP and 2 uCi $^{33}$P-ATP, 50 mM MOPS, 0.1 mM EDTA, 0.1M sucrose, 10 mM MgCl$_2$ plus 0.1% dimethylsulphoxide (containing compound where appropriate) in a total reaction volume of 30 ul. Reactions were incubated at 25° C. for 90 minutes and reactions terminated by addition of EDTA to a final concentration of 50 uM. 10 ul of reaction was spotted to P30 phosphocellulose paper and air dried. Following four washes in ice cold 10% trichloroacetic acid, 0.5% phosphoric acid, papers were air dried prior to addition of liquid scintillant and measurement of radioactivity in a scintillation counter.

Results: The compounds of the examples were found to be effective in inhibiting B-Raf mediated phosphorylation of GST-kdMEK substrate in one or both of the above mentioned assays having IC$_{50}$'s of <3 μM.

The activity of compounds as Raf inhibitors may also be determined by the assays described in WO 99/10325; McDonald, O. B., Chen, W. J., Ellis, B., Hoffman, C., Overton, L., Rink, M., smith, A., Marshall, C. J. and Wood, E. R. (1999) A scintillation proximity assay for the Raf/MEK/ERK kinase cascade: high throughput screening and identification of selective enzyme inhibitors, Anal. Biochem., 268: 318–329 and AACR meeting New Orleans 1998 Poster 3793.

The neuroprotective properties of B-Raf inhibitors may be determined by the following in vitro assay:

Neuroprotective properties of B-Raf Inhibitors in Rat Hippocampal Slice Cultures Organotypic cultures provide an intermediate between dissociated neuronal cell cultures and in-vivo models of oxygen and glucose deprivation (OGD). The majority of glial-neuronal interactions and neuronal circuitry are maintained in cultured hippocampal slices, so facilitating investigation of the patterns of death among differing cell types in a model that resembles the in vivo situation. These cultures allow the study of delayed cellular damage and death 24 hours, or more, post-insult and permit assessment of the consequences of long-term alterations in culture conditions. A number of laboratories have reported delayed neuronal damage in response to OGD in organotypic cultures of the hippocampus (Vornov et al., Stroke, 1994, 25, 57–465; Newell et al., Brain Res., 1995, 676, 38–44). Several classes of compounds have been shown to protect in this model, including EAA antagonists (Strasser et al., Brain Res., 1995, 687, 167–174), Na channel blockers (Tasker et al., J. Neurosci., 1992, 12, 98–4308) and Ca channel blockers (Pringle et al., Stroke, 1996, 7, 2124–2130). To date, relatively little is known of the roles of intracellular kinase mediated signalling pathways in neuronal cell death in this model.

Method: Organotypic hippocampal slice cultures were prepared using the method of Stoppini et al., J. Neurosci. Methods, 1995, 37, 173–182. Briefly, 400 micron sections prepared from hippocampi of 7–8 day postnatal Sprague Dawley rats are cultured on semiporous membranes for 9–12 days. OGD is then induced by incubation in serum and glucose-free medium in an anaerobic chamber for 45 minutes. Cultures are then returned to the air/CO$_2$ incubator for 23 hours before analysis. Propidium iodide (PI) is used as an indicator of cell death. PI is non toxic to neurones and has been used in many studies to ascertain cell viability. In damaged neurons PI enters and binds to nucleic acids. Bound PI shows increased emission at 635 nm when excited at 540 nm. One PI fluorescence image and one white light image are taken and the proportion of cell death analysed. The area of region CA1 is defined from the white light image and superimposed over the PI image. The PI signal is thresholded and area of PI damage expressed as a percentage of the CA1 area. Correlation between PI fluorescence and histologically confirmed cell death has been validated previously by Nissl-staining using cresyl fast violet (Newell et al., J. Neurosci., 1995, 15, 7702–7711).

What is claimed is:
1. A compound of formula (I):

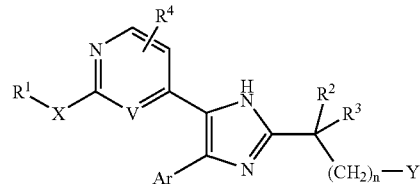

wherein
X is O, CH$_2$, S or NH, or the moiety X—R$^1$ is hydrogen;
V is CH;
R$^1$ is hydrogen, C$_{1-6}$alkyl, aryl, arylC$_{1-6}$alkyl, heterocyclyl, heterocyclylC$_{1-6}$alkyl, heteroaryl, or heteroarylC$_{1-6}$alkyl, any of which except hydrogen may be unsubstituted or substituted;
R$^2$ and R$^3$ independently represent unsubstituted or substituted C$_{1-6}$alkyl, or R$^2$ and R$^3$ together with the carbon atom to which they are attached form an unsubstituted or substituted C$_{3-7}$cycloalkyl or C$_{5-7}$cycloalkenyl ring; or R$^2$ or R$^3$ together with the carbon atom to which they are attached form an unsubstituted or substituted 5 to 7-membered heterocyclyl ring containing up to 3 heteroatoms selected from N, O and S
R$^4$ is hydrogen, X—R$^1$, halogen, unsubstituted or substituted C$_{1-6}$alkylsulfinyl, CH$_2$OR$^5$, di-C$_{1-6}$alkylamino, N(R$^6$)C(O)R$^7$, N(R$^6$)S(O)$_2$R$^8$, or a 5 to 7-membered N-heterocyclyl ring which optionally contains an additional heteroatom selected from O, S and NR$^9$;
Y is NR$^{10}$R$^{11}$, NR$^{10}$C(Z)NR$^{10}$R$^{11}$, NR$^{10}$COOR$^{11}$ or NR$^{10}$SO$_2$R$^{11}$;
Ar is phenyl or a 5- or 6-membered heteroaryl ring either of which may be unsubstituted or substituted;
n is 0, 1, 2, 3 or 4;
R$^5$ is hydrogen, —C(Z)R$^{12}$, unsubstituted or substituted C$_{1-6}$alkyl, unsubstituted or substituted aryl, unsubstituted or substituted arylC$_{1-6}$alkyl, or S(O)$_2$R$^8$;
R$^6$ is hydrogen or C$_{1-6}$alkyl;
R$^7$ is hydrogen, C$_{1-6}$alkyl, C$_{3-7}$cycloalkyl, aryl, arylC$_{1-6}$alkyl, heteroaryl, heteroarylC$_{1-6}$alkyl, heterocyclyl, or heterocyclylC$_{1-6}$alkyl;

R$^8$ is C$_{1-6}$alkyl, C$_{3-7}$cycloalkyl, aryl, arylC$_{1-6}$alkyl, heteroaryl, heteroarylC$_{1-6}$alkyl, heterocyclyl, or heterocyclylC$_{1-6}$alkyl;

R$^9$ is hydrogen, cyano, C$_{1-4}$alkyl, C$_{3-7}$cycloalkyl or aryl;

R$^{10}$, R$^{11}$ and R$^{12}$ are independently selected from hydrogen, C$_{1-6}$alkyl, C$_{3-7}$cycloalkyl, heterocyclyl, heterocyclylC$_{1-6}$alkyl, heterocyclylC$_{2-6}$alkenyl, aryl, arylC$_{1-6}$alkyl, arylC$_{2-6}$alkenyl, heteroaryl, heteroarylC$_{1-6}$alkyl and heteroarylC$_{2-6}$alkenyl any of which may be optionally substituted; or NR$^{10}$R$^{11}$ may represent a 5 to 7-membered heterocyclyl ring optionally containing an additional heteroatom selected from O, n and S; and Z is oxygen or sulfur;

wherein for the substituent or substituents for an alkyl, cycloalkyl, or cycloalkenyl group is/are selected from aryl, heteroaryl, heterocyclyl, C$_{1-6}$alkoxy, halo C$_{1-6}$alkoxy, C$_{1-6}$alkylthio, aryloxy, arylC$_{1-6}$alkoxy, aryl C$_{1-6}$alkylthio, amino, mono- or di-C$_{1-6}$alkylamino, cycloalkyl, cycloalkenyl, carboxy and esters thereof, amide, ureido, guanidino, C$_{1-6}$alkylguanidino, amidina, C$_{1-6}$alkylamidino, C$_{1-6}$acyloxy, azido, hydroxy, and halogen; and wherein the substituent or substituents for an aryl, heterocyclyl or heteroaryl ring is/are selected from halogen, C$_{1-6}$alkyl, aryl, aryl C$_{1-6}$alkyl, C$_{1-6}$alkoxy, C$_{1-6}$alkoxyC$_{1-6}$alkyl, halo C$_{1-6}$alkyl, halo C$_{1-6}$alkoxy, aryloxy, aryl C$_{1-6}$alkoxy, hydroxy, nitro, cyano, azido, amino, mono- and di-N-C$_{1-6}$alkylamino, acylamino, arylcarbonylamino, acyloxy, carboxy, carboxy salts, carboxy esters, carbamoyl, mono- and di-N-C$_{1-6}$alkylcarbamoyl, C$_{1-6}$alkoxycarbonyl, aryloxycarbonyl, ureido, guanidino, C$_{1-6}$alkylguanidino, amidino, C$_{1-6}$alkylamidino, sulphonylamino, aminosulphonyl, C$_{1-6}$alkylthio, C$_{1-6}$alkylsulphinyl, C$_{1-6}$alkylsulphonyl, heterocyclyl, heteroaryl, heterocyclyl C$_{1-6}$alkyl and heteroaryl C$_{1-6}$alkyl; or a pharmaceutically acceptable salt thereof; provided that the compound of formula (I) is not:
  i) [1-[4-(4-fluorophenyl)-5-(4-pyridinyl)-1H-imidazol-2-yl]cyclohexyl]-carbamic acid, phenylmethyl ester; or
  ii) 1-[4-(4-fluorophenyl)-5-(4-pyridinyl)-1H-imidazol-2-yl]-cyclohexanamine.

2. A compound according to claim 1 wherein n is 1.

3. A compound according to claim 1 wherein X—R$^1$ is hydrogen or X—R$^1$ is NH$_2$.

4. A compound according to claim 1 wherein R$^4$ is hydrogen.

5. A compound according to claim 1 wherein Ar is unsubstituted or substituted phenyl.

6. A compound according to claim 5 wherein Ar is substituted by up to 3 substituents independently selected from halo, hydroxy, hydroxy C$_{1-6}$alkyl, and C$_{1-6}$alkoxy.

7. A compound according to claim 6 wherein Ar is 3-hydroxy-4-halophenyl.

8. A compound according to claim 1 wherein R$^2$ and R$^3$ independently represent C$_{1-6}$alkyl, or R$^2$ and R$^3$ together with the carbon atom to which they are attached form an unsubstituted or substituted C$_{3-7}$cycloalkyl ring.

9. A compound according to claim 1 wherein Y is NR$^{10}$R$^{11}$.

10. A compound according to claim 1 wherein R$^{10}$ is hydrogen.

11. A compound according to claim 1 which is:
(2-(4-(4-Chloro-3-methoxy-phenyl)-5-pyridin-4-yl-1H-imidazol-2-yl)-2-methyl-propyl)-carbamic acid tert-butyl ester;
2-(4-(4-Chloro-3-methoxy-phenyl)-5-pyridin-4-yl-1H-imidazol-2-yl)-2-methyl-propylamine;
5-(2-(2-Amino-1,1-dimethyl-ethyl)-5-pyridin-4-yl-1H-imidazol-4-yl)-2-chloro-phenol;
N-(2-(4-(4-Chloro-3-methoxyphenyl)-5-pyridin-4-yl-1H-imidazol-2-yl)-2-methylpropyl)methanesulfonamide;
(2-(4-(3,4-Dihloro-phenyl)-5-pyridin-4-yl-1H-imidazol-2-yl)-2-methyl-propyl)-carbamic acid tert-butyl ester;
2-(4-(3,4-Dichloro-phenyl)-5-pyridin-4-yl-1H-imidazol-2-yl)-2-methyl-propylamine;
1-(2-(4-(4-Chloro-3-hydroxy-phenyl)-5-pyridin-4-yl-1H-imidazol-2-yl)-2-methyl-propyl)-3-(4-chlorophenyl)-urea;
1-(2-(4-(3,4-Dichloro-phenyl)-5-pyridin-4-yl-1H-imidazol-2-yl)-2-methyl-propyl)-3-(4-chlorophenyl)-urea;
5-(2-(2-Benzylamino-1,1-dimethyl-ethyl)-5-pyridin-4-yl-1H-imidazol-4-yl)-2-chloro-phenol;
Benzyl-(2-(4-(3,4-dichoro-phenyl)-5-pyridin-4-yl-1H-imidazol-2-yl)-2-methyl-propyl)-amine;
N-(2-(4-(3,4-Dichloro-phenyl)-5-pyridin-4-yl-1H-imidazol-2-yl)-2-methylpropyl)methanesulfonamide;
2-Chloro-5-{2-[2-(4-methoxy-benzylamino)-1,1-dimethyl-ethyl]-5-pyridin-4-yl-1H-imidazol-4-yl}-phenol;
2-Chloro-5-{2-[2-(4-chloro-benzylamino)-1,1-dimethyl-ethyl]-5-pyridin-4-yl-1H-imidazol-4-yl}-phenol;
2-Chloro-5-{2-[2-(2,2-dimethyl-propylamino)-1,1-dimethyl-ethyl]-5-pyridin-4-yl-1H-imidazol-4-yl}-phenol;
2-Chloro-5-(2-{2-[3-(4-dimethylamino-phenyl)-allylamino]-1,1-dimethyl-ethyl}-5-pyridin-4-yl-1H-imidazol-4-yl)-phenol;
2-Chloro-5-[2-(1,1-dimethyl-2-pentylamino-ethyl)-5-pyridin-4-yl-1H-imidazol-4-yl]-phenol;
2-Chloro-5-(2-{2-[4-(3-dimethylamino-propoxy)-benzylamino]-1,1-dimethyl-ethyl}-5-pyridin-4-yl-1H-imidazol-4-yl)-phenol;
2-Chloro-5-{2-[2-(3,4-difluorobenzylamino)-1,1-dimethyl-ethyl]-5-pyridin-4-yl-1H-imidazol-4-yl}-phenol;
2-Chloro-5-{2-[2-(3-methoxy-benzylamino)-1,1-dimethyl-ethyl]-5-pyridin-4-yl-1H-imidazol-4-yl}-phenol;
2-Chloro-5-{2-[2-(3,4-dichloro-benzylamino)-1,1-dimethyl-ethyl]-5-pyridin-4-yl-1H-imidazol-4-yl}-phenol;
2-Chloro-5-{2-[2-(4-methanesulfonyl-benzylamino)-1,1-dimethyl-ethyl]-5-pyridin-4-yl-1H-imidazol-4-yl}-phenol;
2-Chloro-5-{2-[1,1-dimethyl-2-(4-trifluoromethyl-benzylamino)-ethyl]-5-pyridin-4-yl-1H-imidazol-4-yl}-phenol;
2-Chloro-5-(2-{2-[(furan-3-ylmethyl)amino]-1,1-dimethyl-ethyl}-5-pyridin-4-yl-1H-imidazol-4-yl)-phenol;
2-Chloro-5-(2-{1,1-dimethyl-2-[(1-methyl-1H-pyrrol-2-ylmethyl)-amino]-ethyl}-5-pyridin-4-yl-1H-imidazol-4-yl)-phenol;
2-Chloro-5-(2-{1,1-dimethyl-2-[(thiazol-2-ylmethyl)-amino]-ethyl}-5-pyridin-4-yl-1H-imidazol-4-yl)-phenol;
2-Chloro-5-(2-{1,1-dimethyl-2-[(thiophen-2-ylmethyl)-amino]-ethyl}-5-pyridin-4-yl-1H-imidazol-4-yl)-phenol;
2-Chloro-5-{2-[1,1-dimethyl-2-(4-pyrrolidin-1-yl-benzylamino)-ethyl]-5-pyridin-4-yl-1H-imidazol-4-yl}-phenol;
2-Chloro-5-(2-{1,1-dimethyl-2-[(pyridin-3-ylmethyl)-amino]-ethyl}-5-pyridin-4-yl-1H-imidazol-4-yl)-phenol;
2-Chloro-5-(2-{2-[(1H-imidazol-2-ylmethyl)-amino]-1,1-dimethyl-ethyl}-5-pyridin-4-yl-1H-imidazol-4-yl)-phenol;
2-Chloro-5-{2-[1,1-dimethyl-2-(4-trifluoromethoxy-benzylamino)-ethyl]-5-pyridin-4-yl-1H-imidazol-4-yl}-phenol;
2-Chloro-5-(2-{2-[1-(2-methoxy-ethyl)-piperidin-4-ylamino]-1,1-dimethyl-ethyl}-5-pyridin-4-yl-1H-imidazol-4-yl)-phenol;

2-Chloro-5-[2-(2-{[1-(2-methoxy-ethyl)-piperidin-4-yl-methyl]-amino}-1,1-dimethyl-ethyl)-5-pyridin-4-yl-1H-imidazol-4-yl]-phenol;
2-Chloro-5-{2-[2-(2-methoxy-ethylamino)-1,1-dimethyl-ethyl]-5-pyridin-4-yl-1H-imidazol-4-yl}-phenol;
2-Chloro-5-{2-[2-(5-hydroxy-pentylamino)-1,1-dimethyl-ethyl]-5-pyridin-4-yl-1H-imidazol-4-yl}-phenol;
2-Chloro-5-[2-(1,1-dimethyl-2-morpholin-4-yl-ethyl)-5-pyridin-4-yl-1H-imidazol-4-yl]-phenol;
N-{2-[4-(4-Chloro-3-hydroxy-phenyl)-5-pyridin-4-yl-1H-imidazol-2-yl]-2-methyl-propyl}-benzenesulfonamide;
4-{2-[4-(4-Chloro-3-hydroxy-phenyl)-5-pyridin-4-yl-1H-imidazol-2-yl]-2-methyl-propylsulfamoyl}-benzoic acid;
5-{2-[4-(4-Chloro-3-hydroxy-phenyl)-5-pyridin-4-yl-1H-imidazol-2-yl]-2-methyl-propylsulfamoyl}-2-hydroxy-benzoic acid;
N-{2-[4-(4-Chloro-3-hydroxy-phenyl)-5-pyridin-4-yl-1H-imidazol-2-yl]-2-methyl-propyl}-4-cyano-benzenesulfonamide;
N-{2-[4-(4-Chloro-3-hydroxy-phenyl)-5-pyridin-4-yl-1H-imidazol-2-yl]-2-methyl-propyl}-1-phenyl-methanesulfonamide;
4-Aminomethyl-N-{2-[4-(4-chloro-3-hydroxy-phenyl)-5-pyridin-4-yl-1H-imidazol-2-yl]-2-methyl-propyl}-benzenesulfonamide;
2-(4-Methyl-piperazin-1-yl)-ethanesulfonic acid {2-[4-(4-chloro-3-hydroxy-phenyl)-5-pyridin-4-yl-1H-imidazol-2-yl]-2-methyl-propyl}-amide;
2-Morpholin-4-yl-ethanesulfonic acid {2-[4-(4-chloro-3-hydroxy-phenyl)-5-pyridin-4-yl-1H-imidazol-2-yl]-2-methyl-propyl}-amide;
1-{2-[4-(4-Chloro-3-hydroxy-phenyl)-5-pyridin-4-yl-1H-imidazol-2-yl]-2-methyl-propyl}-3-phenyl-urea;
1-{2-[4-(4-Chloro-3-hydroxy-phenyl)-5-pyridin-4-yl-1H-imidazol-2-yl]-2-methyl-propyl}-3-(3-morpholin-4-yl-propyl)-urea;
1-{2-[4-(4-Chloro-3-hydroxy-phenyl)-5-pyridin-4-yl-1H-imidazol-2-yl]-2-methyl-propyl}-3-[4-(2-dimethylamino-ethoxy)-phenyl]-urea;
1-{2-[4-(4-Chloro-3-hydroxy-phenyl)-5-pyridin-4-yl-1H-imidazol-2-yl]-2-methyl-propyl}-3-[4-methoxy-3-(4-methyl-piperazin-1-yl)-phenyl]-urea;
1-{2-[4-(4-Chloro-3-hydroxy-phenyl)-5-pyridin-4-yl-1H-imidazol-2-yl]-2-methyl-propyl}-3-[3-methoxy-4-(2-morpholin-4-yl-ethoxy)-phenyl]-urea;
4-(2-Methoxy-ethyl)-piperazine-1-carboxylic acid {2-[4-(4-chloro-3-hydroxy-phenyl)-5-pyridin-4-yl-1H-imidazol-2-yl]-2-methyl-propyl}-amide;
5-[2-(2-Amino-1,1-dimethyl-ethyl)-5-pyridin-4-yl-1H-imidazol-4-yl]-2-bromo-phenol;
N-{2-[4-(4-Bromo-3-hydroxy-phenyl)-5-pyridin-4-yl-1H-imidazol-2-yl]-2-methyl-propyl}-methanesulfonamide;
2-Chloro-5-[2-(1,1-dimethyl-2-methylamino-ethyl)-5-pyridin-4-yl-1H-imidazol-4-yl]-phenol;
2-Chloro-5-{[(furan-3-ylmethyl-methyl-amino)-dimethyl-ethyl]pyridin-4-yl-1H-imidazol-4-yl}-phenol;
2-Chloro-5-{[dimethyl-(methyl-pentyl-amino)ethyl]-pyridin-4-yl-1H-imidazol-4-yl}-phenol;
2-Chloro-5-[({[1-(2-methoxy-ethyl)-piperidin-4-yl]-methyl-amino}-dimethyl-ethyl)-pyridin-4-yl-1H-imidazol-4-yl]-phenol;
2-Chloro-5-[({[1-(2-methoxy-ethyl)-piperidin-4-ylmethyl]-methyl-amino}-dimethyl-ethyl)-pyridin-4-yl-1H-imidazol-4-yl]-phenol;
2-Chloro-5-({[(2-methoxy-ethyl)-methyl-amino]-dimethyl-ethyl}-pyridin-4-yl-1H-imidazol-4-yl)-phenol;
2-Chloro-5-{2-[2-benzylmethyl-methyl-amino)-1,1-dimethyl-ethyl]-pyridin-4-yl-1H-imidazol-4-yl}-phenol;
2-Chloro-5-({[(2-hydroxy-ethyl)-methyl-amino]-dimethyl-ethyl}-pyridin-4-yl-1H-imidazol-4-yl)-phenol trihydrochloride;
4-(2-Methoxy-ethyl)-piperazine-1-carboxylic acid {2-[4-(4-chloro-3-hydroxy-phenyl)-5-pyridin-4-yl-1H-imidazol-2-yl]-2-methyl-propyl}-methyl-amide;
5-[2-(1-Aminomethyl-cyclohexyl)-5-pyridin-4-yl-1H-imidazol-4-yl]-2-chloro-phenol;
2-Chloro-5-(2-{1-[4-chloro-benzylamino)-methyl]-cyclohexyl}-5-pyridin-4-yl-1H-imidazol-4-yl)-phenol;
5-[2-(1-Amino-1-methyl-ethyl)-5-pyridin-4-yl-1H-imidazol-4-yl]-2-chloro-phenol;
N-{1-[4-(4-Chloro-3-hydroxy-phenyl)-5-pyridin-4-yl-1H-imidazol-2-yl]-1-methyl-ethyl}-methanesulfonamide;
2-Chloro-5-{2-[1-(4-methoxy-benzylamino)-1-methyl-ethyl]-5-pyridin-4-yl-1H-imidazol-4-yl}-phenol;
2-Chloro-5-{2-[1-(3-methoxy-benzylamino)-1-methyl-ethyl]-5-pyridin-4-yl-1H-imidazol-4-yl}-phenol;
2-Chloro-5-{2-[1-(3,4-dichloro-benzylamino)-1-methyl-ethyl]-5-pyridin-4-yl-1H-imidazol-4-yl}-phenol;
2-Chloro-5-{2-[1-(4-methanesulfonyl-benzylamino)-1-methyl-ethyl]-5-pyridin-4-yl-1H-imidazol-4-yl}-phenol;
2-Chloro-5-{2-[1-(4-trifluoromethyl-benzylamino)-1-methyl-ethyl]-5-pyridin-4-yl-1H-imidazol-4-yl}-phenol;
2-Chloro-5-{2-[1-methyl-1-(4-pyrrolidin-1-yl-benzylamino)-1-methyl-ethyl]-5-pyridin-4-yl-1H-imidazol-4-yl}-phenol;
N-[4-({1-[4-Chloro-3-hydroxy-phenyl)-5-pyridin-4-yl-1H-imidazol-2-yl]-1-methyl-ethylamino}-methyl)-phenyl]-acetamide;
2-Chloro-5-(2-{1-[(furan-3-ylmethyl)-amino]-1-methyl-ethyl}-5-pyridin-4-yl-1H-imidazol-4-yl)-phenol;
2-Chloro-5-(2-{1-methyl-1-[(pyridin-3-ylmethyl)-amino]-ethyl}-5-pyridin-4-yl-1H-imidazol-4-yl)-phenol;
2-Chloro-5-(2-{1-[(1H-imidazol-2-ylmethyl)-amino]-1-methyl-ethyl}-5-pyridin-4-yl-1H-imidazol-4-yl)-phenol;
2-Chloro-5-(2-{1-methyl-1-[(thiazol-2-ylmethyl)-amino]-ethyl}-5-pyridin-4-yl-1H-imidazol-4-yl)-phenol;
2-Chloro-5-(2-{1-methyl-1-[(thiophen-2-ylmethyl)-amino]-ethyl}-5-pyridin-4-yl-1H-imidazol-4-yl)-phenol;
2-Chloro-5-{2-[1-methyl-1-(4-trifluoromethoxy-benzylamino)-ethyl]-5-pyridin-4-yl-1H-imidazol-4-yl}-phenol;
1-{1-[4-(4-Chloro-3-hydroxy-phenyl)-5-pyridin-4-yl-1H-imidazol-2-yl]-1-methyl-ethyl}-3-phenyl-urea;
1-{1-[4-(4-Chloro-3-hydroxy-phenyl)-5-pyridin-4-yl-1H-imidazol-2-yl]-1-methyl-ethyl}-3-[4-(2-dimethylamino-ethoxy)-phenyl]-urea;
1-{1-[4-(4-Chloro-3-hydroxy-phenyl)-5-pyridin-4-yl-1H-imidazol-2-yl]-1-methyl-ethyl}-3-[4-methoxy-3-(4-methyl-piperazin-1-yl)-phenyl]-urea;
1-{1-[4-(4-Chloro-3-hydroxy-phenyl)-5-pyridin-4-yl-1H-imidazol-2-yl]-1-methyl-ethyl}-3-[3-methoxy-4-(2-morpholin-4-yl-ethoxy)-phenyl]-urea;

or a pharmaceutically acceptable derivative thereof.

12. A pharmaceutical composition comprising a compound according to claim 1 or a pharmaceutically acceptable salt thereof and a pharmaceutically acceptable carrier.

\* \* \* \* \*